US008618358B2

(12) United States Patent
Feng et al.

(10) Patent No.: US 8,618,358 B2
(45) Date of Patent: Dec. 31, 2013

(54) TRANSGENIC MAIZE EVENT MON 87427 AND THE RELATIVE DEVELOPMENT SCALE

(75) Inventors: Paul C. C. Feng, Wildwood, MO (US); Agustin E. Fonseca, St. Louis, MO (US); Carl W. Garnaat, Eureka, MO (US); Oscar Heredia, High Hill, MO (US); Jintai Huang, Chesterfield, MO (US); Rebecca A. Kelly, South Kingston, RI (US); Youlin Qi, Chesterfield, MO (US); Martin A. Stoecker, Wentzville, MO (US)

(73) Assignee: Monsanto Technology LLC, St. Louis, MO (US)

( * ) Notice: Subject to any disclaimer, the term of this patent is extended or adjusted under 35 U.S.C. 154(b) by 291 days.

(21) Appl. No.: 12/947,454

(22) Filed: Nov. 16, 2010

(65) Prior Publication Data

US 2011/0126310 A1 May 26, 2011

Related U.S. Application Data

(60) Provisional application No. 61/263,526, filed on Nov. 23, 2009, provisional application No. 61/263,530, filed on Nov. 23, 2009.

(51) Int. Cl.
*C12N 15/82* (2006.01)
*C12N 15/52* (2006.01)
*C12N 15/11* (2006.01)
*C12Q 1/68* (2006.01)
*A01H 9/00* (2006.01)

(52) U.S. Cl.
USPC ........ 800/300; 536/24.3; 435/6.1; 435/252.3; 800/320.1; 800/295; 800/266

(58) Field of Classification Search
None
See application file for complete search history.

(56) References Cited

U.S. PATENT DOCUMENTS

| | | | |
|---|---|---|---|
| 6,448,476 B1 | 9/2002 | Barry | |
| 6,762,344 B1 | 7/2004 | Spencer et al. | |
| 6,825,400 B2 | 11/2004 | Behr et al. | |
| 7,306,909 B2 | 12/2007 | Krieb et al. | |
| 7,314,970 B2 | 1/2008 | Spencer et al. | |
| 7,491,813 B2 | 2/2009 | Wu et al. | |
| 7,554,012 B2 | 6/2009 | Barry | |
| 8,212,113 B2 * | 7/2012 | Beazley et al. ............ | 800/300.1 |
| 2003/0106096 A1 | 6/2003 | Barry | |
| 2004/0034888 A1 | 2/2004 | Liu et al. | |
| 2007/0130645 A1 | 6/2007 | Wu et al. | |
| 2009/0165166 A1 | 6/2009 | Feng et al. | |

FOREIGN PATENT DOCUMENTS

EP 0 975 778 B1 6/2007
WO WO 2009/085982 A1 7/2009
WO WO 2010/117735 A1 10/2010
WO WO 2010/117737 A8 10/2010

OTHER PUBLICATIONS

Privalle et al, Development of an Agricultural Biotechnology Crop Product: Testing from Discovery to Commercialization, J. of Agric. and Food Chem. (2012) 10179-10187.*
Puchta et al, From centiMorgans to Base Pairs: Homologous Recombination in Plants, Trends in Plant Sci. (1996) 1:340-348.*
Devine, M., Why are there not more herbicide-tolerant crops?, Pest Mgmt. Sci. (2005) 61:312-317.*
New England BioLabs Inc. 1998/99 Catalog, (NEB Catalog) , pp. 121 and 284, undated.
Final Office Action regarding U.S. Appl. No. 11/801,114, dated Aug. 26, 2009.
Sequence Alignment between SEQ ID No. 10 in U.S. Appl. No. 12/947,454 and SEQ ID No. 9257 in U.S. Publication No. 2007/0130645 A1, undated.
Fiscal Year 2008 Proposals, University of Arkansas, Fayetteville, Arkansas, undated.
Fiscal Year 2009 Awards, University of Arkansas, Fayetteville, Arkansas, p. 3, undated.
Fraley et al., "Expression of bacterial genes in plant cells," *Proc. Natl. Acad. Sci.*, 80:4803-4807, Aug. 1983.
Windels et al., "Development of a line specific GMO detection method: A case study," *Med. Fac. Landbouww. Univ. Gent.*, 64(5)(b):459-464, 1999.
Database ENA, "*Brassica napus* clone JBr037K23," Accession No. AC236899, 2009.
Database ENA, "*Oryza sativa* Japonica Group transgenic plant p0282 integrated T-DNA(Ds), flanking sequence," Accession No. AF463856, 2003.
Database ENA, "OG2AR19TH ZM_0.7_1.5_KB Zea mays genomic clone ZMMBMa0747C14, genomic survey sequence," Accession No. CG220210, 2003.
Information regarding previously reference WO 2009/085982, which discloses event GHS1, referring to the same event as MON 87427 of the present invention, provided in the Transmittal Letter filed Jul. 18, 2013.

* cited by examiner

*Primary Examiner* — David H Kruse
*Assistant Examiner* — Mykola Kovalenko
(74) *Attorney, Agent, or Firm* — Dentons US LLP; Pamela Sisson

(57) ABSTRACT

The invention provides transgenic maize event MON 87427 and plants, plant cells, seeds, plant parts, and commodity products derived from event MON 87427. The invention also provides nucleotides specific for transgenic maize event MON 87427 and plants, plant cells, seeds, plant parts, and commodity products comprising nucleotides specific for transgenic maize event MON 87427. The invention also provides methods related to transgenic maize event MON 87427 and to the Roundup® Hybridization System (RHS). The invention also provides a Relative Development Scale useful for monitoring and determining reproductive development in maize that reconciles developmental differences across various maize varieties. This is useful for determining the optimal timing of a treatment regimen in which tassel development stage is an important factor, including various methods in making hybrid seed.

29 Claims, 9 Drawing Sheets

SEQUENCE LISTING

```
<160> NUMBER OF SEQ ID NOS: 19

<210> SEQ ID NO 1
<211> LENGTH: 20
<212> TYPE: DNA
```

<213> ORGANISM: Artificial Sequence
<220> FEATURE:
<223> OTHER INFORMATION: artifical DNA sequence comprising corn genomic
    sequence and transgene sequence

<400> SEQUENCE: 1
aatcgggaca atatggagaa                                               20

<210> SEQ ID NO 2
<211> LENGTH: 20
<212> TYPE: DNA
<213> ORGANISM: Artificial Sequence
<220> FEATURE:
<223> OTHER INFORMATION: artifical DNA sequence comprising corn genomic
    sequence and transgene sequence

<400> SEQUENCE: 2
catgcaagtt gcaacgcggc                                               20

<210> SEQ ID NO 3
<211> LENGTH: 60
<212> TYPE: DNA
<213> ORGANISM: Artificial Sequence
<220> FEATURE:
<223> OTHER INFORMATION: artifical DNA sequence comprising corn genomic
    sequence and transgene sequence

<400> SEQUENCE: 3
cggtcgggtc aaatgtagaa aatcgggaca atatggagaa aaagaaagag taattaccaa   60

<210> SEQ ID NO 4
<211> LENGTH: 60
<212> TYPE: DNA
<213> ORGANISM: Artificial Sequence
<220> FEATURE:
<223> OTHER INFORMATION: artifical DNA sequence comprising corn genomic
    sequence and transgene sequence

<400> SEQUENCE: 4
tatcagcttg ttggaagtta catgcaagtt gcaacgcggc agccgccagc ggcgcggagc   60

<210> SEQ ID NO 5
<211> LENGTH: 100
<212> TYPE: DNA
<213> ORGANISM: Artificial Sequence
<220> FEATURE:
<223> OTHER INFORMATION: artifical DNA sequence comprising corn genomic
    sequence and transgene sequence

<400> SEQUENCE: 5 tttttcgta aatacggaaa cggtcgggtc aaatgtagaa aatcgggaca atatggagaa    60
aaagaaagag taattaccaa tatggagaaa accgggaaat                         100

<210> SEQ ID NO 6
<211> LENGTH: 100
<212> TYPE: DNA
<213> ORGANISM: Artificial Sequence
<220> FEATURE:
<223> OTHER INFORMATION: artifical DNA sequence comprising corn genomic
    sequence and transgene sequence

<400> SEQUENCE: 6
ttcccgcctt cagtttaaac tatcagcttg ttggaagtta catgcaagtt gcaacgcggc   60
agccgccagc ggcgcggagc gacgaaacga aacgtgcgcg                         100

<210> SEQ ID NO 7

```
<211> LENGTH: 972
<212> TYPE: DNA
<213> ORGANISM: Artificial Sequence
<220> FEATURE:
<223> OTHER INFORMATION: artifical DNA sequence comprising corn genomic
      sequence and transgene sequence

<400> SEQUENCE: 7
tagttagggt tatgtgggca aataccgact ttgcccctga ggggtctcac atctctatat      60
aaggaacctg tacatccctt cataatacag agatcagaaa gaggccagag gcccaaccct    120
atatccagtg tctcgtgtgt ttcttctgtc gtgcttatga aaagggagac gggtctctcta   180 catcttcttg cgcctctact gctgacggga gggaagggag cggatctggt gatccgtggt    240
aacgtagttc tcaacactag aaataaaaga gtaggccaa gatgaactgg gcctcttgct     300
gggcccccaa gtctctgacg cagaaacgac ctcccaccgt tccgcgccgt caggccagtt    360
cagattcaga catagggatg aaaacagacg gaaacggacg gaaaaacccc tctcctgttt    420
ccgtatccgc attttatcat cggaaacggg atcaggtccg gaatagtcgg gaacggaaac    480
gggagcggga taaacggaat tgcgaaaacg aacggaaaca gaaatactaa cggaaagtca    540
taatttaata taaatagaaa tgttattgat gtttgactag tgattgattg acagaacaat    600
aacataaaac aaatagatat agagagacaa cattctattg ttgtttggtt gctaaatgtg    660
tacatttagc tacatccgat gttgtttaag actttagatc acctgtcatt tgaaaacagc    720
cggtggttat aatgacaaat tatgctataa tttgtcacct aaatacacga ggatttagtt    780
tatatactaa tgcatattag ctcgtcccat atttgtcaaa tacggaataa atacgggttc    840
aatccggaaa aaacgggat ctcgcaaaaa cggacggaat aagtcctctc ccgtttccgt     900
cccattttca tattttttcg taaatacgga aacggtcggg tcaaatgtag aaaatcggga    960
caatatggag aa                                                        972

<210> SEQ ID NO 8
<211> LENGTH: 1078
<212> TYPE: DNA
<213> ORGANISM: Artificial Sequence
<220> FEATURE:
<223> OTHER INFORMATION: artifical DNA sequence comprising corn genomic
      sequence and transgene sequence

<400> SEQUENCE: 8
catgcaagtt gcaacgcggc agccgccagc ggcgcggagc gacgaaacga acgtgcgcg      60 cggctggtcc tagaggggcg gttgcaactt gcatgtaact tccacgcgac cgcaggcgtg    120
cgtgcgtcac gactcgcgtc gtagcctctc gtcactcgcg ttcggcttcc gctcgggggc    180
gcgaatcttc tcgacccatc gaggcaagaa acccaagcct aatccgaccc gccatggctt    240
tccttgcttg ctccccccc ccttatcttc ccgcgggtag tatataatca tcccctccgc     300
cgggctcgct tccttgcgca accatccaat ccaatcgaac caccagtcca ccacctgatt    360
gactagagca aaagcacaag ccgcccacgc atctcgattg cagcagcagc agcagcagca    420
gaagcggcgc gcagagctcg tgacgagagc aaccttcctt ccgttcctcg atcgccatgg    480
acaaggtgct agccttctcg atcctgagcg cgtcgccggc cgacctctcc tccgcgggcg    540
ccggcttcgg cgggagctgg gcgcggctgt cgtggcggag gggcgcggac gaccagcgtg    600
cgccgcggcg ggagcagcag cagcggcagg aggaggagga cagggagaag cgagacccgc    660
gctcccgcga cggcgcgcg cacgcgagcg gaggggagc ggcggcggcg ccgccgccac      720
cgcggttcgc gccggagttt gacgggatcg actggttcgg aaccatcgtg tcgcgctgat    780
```

```
caacaatccg ggctcggccg acgcgccccc cgagttaacc acgtgaccaa tcctgtctac      840
tggagtatgt ttttacctg atggtggatt aattgtccca acacagataa ttgggactcc      900
gcgtgttgta catacaggga actgctcact tatcaggggg ggatggggaa catttatttg      960
ttcctgtcct ctgcattttt tttcctgtac cgaaatggat ggatggtctc caattcgaaa     1020
ccgagtcctg cagctccagg taatctgccg gtggatgaac ccaagccgaa ctgtcccg       1078
```

<210> SEQ ID NO 9
<211> LENGTH: 3746
<212> TYPE: DNA
<213> ORGANISM: Artificial Sequence
<220> FEATURE:
<223> OTHER INFORMATION: artifical DNA sequence comprising corn genomic
      sequence and transgene sequence

<400> SEQUENCE: 9

```
atatggagaa aaagaaagag taattaccaa tatggagaaa accgggaaat ctacatggat       60
cagcaatgag tatgatggtc aatatggaga aaaagaaaga gtaattacca attttttttc      120
aattcaaaaa tgtagatgtc cgcagcgtta ttataaaatg aaagtacatt ttgataaaac      180
gacaaattac gatccgtcgt atttataggc gaaagcaata aacaaattat tctaattcgg      240
aaatctttat ttcgacgtgt ctacattcac gtccaaatgg gggcttagat gagaaacttc      300
acgatcgatg cggccgcgtt aacaagcttc tgcaggtccg attgagactt ttcaacaaag      360
ggtaatatcc ggaaacctcc tcggattcca ttgcccagct atctgtcact ttattgtgaa      420
gatagtggaa aaggaaggtg gctcctacaa atgccatcat tgcgataaag gaaaggccat      480
cgttgaagat gcctctgccg acagtggtcc caaagatgga cccccaccca cgaggagcat      540
cgtggaaaaa gaagacgttc caaccacgtc ttcaaagcaa gtggattgat gtgatggtcc      600
gattgagact tttcaacaaa gggtaatatc cggaaacctc ctcggattcc attgcccagc      660
tatctgtcac tttattgtga agatagtgga aaaggaaggt ggctcctaca atgccatca      720 ttgcgataaa ggaaaggcca tcgttgaaga tgcctctgcc gacagtggtc ccaaagatgg      780 accccccaccc acgaggagca tcgtggaaaa agaagacgtt ccaaccacgt cttcaaagca     840
agtggattga tgtgatatct ccactgacgt aagggatgac gcacaatccc actatccttc      900
gcaagaccct tcctctatat aaggaagttc atttcatttg gagaggacac gctgacaagc      960
tgactctagc agatctaccg tcttcggtac gcgctcactc cgccctctgc ctttgttact     1020
gccacgtttc tctgaatgct ctcttgtgtg tgattgctg agagtggttt agctggatct      1080
agaattacac tctgaaatcg tgttctgcct gtgctgatta cttgccgtcc tttgtagcag     1140
caaaatatag ggacatggta gtacgaaacg aagatagaac ctacacagca atacgagaaa     1200
tgtgtaattt ggtgcttagc ggtatttatt taagcacatg ttggtgttat agggcacttg     1260
gattcagaag tttgctgtta atttaggcac aggcttcata ctacatgggt caatagtata     1320
gggattcata ttataggcga tactataata atttgttcgt ctgcagagct tattatttgc     1380
caaaattaga tattcctatt ctgttttttgt ttgtgtgctg ttaaattgtt aacgcctgaa     1440
ggaataaata taaatgacga aatttgatg tttatctctg ctcctttatt gtgaccataa      1500
gtcaagatca gatgcacttg ttttaaatat tgttgtctga agaaataagt actgacagta     1560
ttttgatgca ttgatctgct tgtttgttgt aacaaaattt aaaaataaag agtttccttt     1620
ttgttgctct ccttacctcc tgatggtatc tagtatctac caactgacac tatattgctt     1680
ctctttacat acgtatcttg ctcgatgcct tctccctagt gttgaccagt gttactcaca     1740
tagtctttgc tcatttcatt gtaatgcaga taccaagcgg cctctagagg atccaggagc     1800
```

```
aaccatggcg caagttagca gaatctgcaa tggtgtgcag aacccatctc ttatctccaa   1860
tctctcgaaa tccagtcaac gcaaatctcc cttatcggtt tctctgaaga cgcagcagca   1920
tccacgagct tatccgattt cgtcgtcgtg gggattgaag aagagtggga tgacgttaat   1980
tggctctgag cttcgtcctc ttaaggtcat gtcttctgtt tccacggcgt gcatgctaca   2040
cggtgcaagc agccggccgg caaccgctcg caaatcttcc ggcctttcgg aacggtcag    2100 gattccgggc gataagtcca tatcccaccg gtcgttcatg ttcggcggtc ttgccagcgg   2160
tgagacgcgc atcacgggcc tgcttgaagg tgaggacgtg atcaataccg gaaggccat    2220 gcaggctatg ggagcgcgta tccgcaagga aggtgacaca tggatcattg acggcgttgg   2280
gaatggcggt ctgctcgccc tgaggcccc tctcgacttc ggcaatgcgg cgacgggctg    2340
caggctcact atgggactgg tcggggtgta cgacttcgat agcacgttca tcggagacgc   2400
ctcgctcaca aagcgcccaa tgggccgcgt tctgaacccg ttgcgcgaga tgggcgtaca   2460
ggtcaaatcc gaggatggtg accgtttgcc cgttacgctg cgcgggccga agacgcctac   2520
cccgattacc taccgcgtgc caatggcatc cgcccaggtc aagtcagccg tgctcctcgc   2580
cggactgaac actccgggca tcaccacggt gatcgagccc atcatgacca gggatcatac   2640
cgaaaagatg cttcaggggt ttggcgccaa cctgacggtc gagacggacg ctgacggcgt   2700
caggaccatc cgccttgagg gcaggggtaa actgactggc caagtcatcg atgttccggg   2760
agacccgtcg tccacggcct tcccgttggt tgcggcgctg ctcgtgccgg ggagtgacgt   2820
gaccatcctg aacgtcctca tgaacccgac caggaccggc ctgatcctca cgcttcagga   2880
gatgggagcc gacatcgagg tgatcaaccc gcgcctggca ggcggtgaag acgttgcgga   2940
tctgcgcgtg cgctcctcta ccctgaaggg cgtgacggtc ccggaagatc gcgcgccgtc   3000
catgatagac gagtatccta ttctggccgt cgccgctgcg ttcgccgaag gggccacggt   3060
catgaacggt cttgaggaac tccgcgtgaa ggaatcggat cgcctgtcgg cggtggccaa   3120
tggcctgaag ctcaacggtg ttgactgcga cgagggtgag acctcactcg tggtccgtgg   3180
ccggcctgat ggcaagggcc tcggcaacgc cagtggagcg gccgtcgcca cgcacctcga   3240
tcatcgcatc gcgatgtcct tcttggtgat gggtctcgtc tcagagaacc cggtgaccgt   3300
cgatgacgcc acgatgatag cgacgagctt cccagagttc atggatctga tggcgggcct   3360
cggggccaag atcgaactgt ctgacacgaa ggccgcttga attcccgatc gttcaaacat   3420
ttggcaataa agtttcttaa gattgaatcc tgttgccggt cttgcgatga ttatcatata   3480
atttctgttg aattacgtta agcatgtaat aattaacatg taatgcatga cgttatttat   3540
gagatgggtt tttatgatta gagtcccgca attatacatt taatacgcga tagaaaacaa   3600
aatatagcgc gcaaactagg ataaattatc gcgcgcggtg tcatctatgt tactagatcg   3660
gggatatccc cagcttgatg gggatcagat tgtcgtttcc cgccttcagt ttaaactatc   3720
agcttgttgg aagttacatg caagtt                                        3746
```

<210> SEQ ID NO 10
<211> LENGTH: 5776
<212> TYPE: DNA
<213> ORGANISM: Artificial Sequence
<220> FEATURE:
<223> OTHER INFORMATION: artifical DNA sequence comprising corn genomic
      sequence and transgene sequence

<400> SEQUENCE: 10

```
tagttagggt tatgtgggca aataccgact ttgcccctga ggggtctcac atctctatat    60
```

```
aaggaacctg tacatccctt cataatacag agatcagaaa gaggccagag gcccaaccct    120
atatccagtg tctcgtgtgt ttcttctgtc gtgcttatga aaagggagac gggttctcta    180
catcttcttg cgcctctact gctgacggga gggaagggag cggatctggt gatccgtggt    240
aacgtagttc tcaacactag aaataaaaga agtaggccaa gatgaactgg gcctcttgct    300
gggcccccaa gtctctgacg cagaaacgac ctcccaccgt tccgcgccgt caggccagtt    360
cagattcaga catagggatg aaaacagacg gaaacgacg gaaaaacccc tctcctgttt    420
ccgtatccgc attttatcat cggaaacggg atcaggtccg gaatagtcgg gaacggaaac    480
gggagcggga taaacggaat tgcgaaaacg aacggaaaca gaaatactaa cggaaagtca    540
taatttaata taaatagaaa tgttattgat gtttgactag tgattgattg acagaacaat    600
aacataaaac aaatagatat agagagacaa cattctattg ttgtttggtt gctaaatgtg    660
tacatttagc tacatccgat gttgtttaag actttagatc acctgtcatt tgaaaacagc    720
cggtggttat aatgacaaat tatgctataa tttgtcacct aaatacacga ggatttagtt    780
tatatactaa tgcatattag ctcgtcccat atttgtcaaa tacggaataa atacgggttc    840
aatccggaaa aaacgggat ctcgcaaaaa cggacggaat aagtcctctc cgtttccgt    900 cccattttca tatttttcg taaatacgga aacggtcggg tcaaatgtag aaaatcggga    960
caatatggag aaaagaaag agtaattacc aatatggaga aaccgggaa atctacatgg    1020 atcagcaatg agtatgatgg tcaatatgga gaaaagaaa gagtaattac caatttttt    1080 tcaattcaaa aatgtagatg tccgcagcgt tattataaaa tgaaagtaca ttttgataaa    1140
acgacaaatt acgatccgtc gtatttatag gcgaaagcaa taaacaaatt attctaattc    1200
ggaaatcttt atttcgacgt gtctacattc acgtccaaat gggggcttag atgagaaact    1260
tcacgatcga tgcggccgcg ttaacaagct tctgcaggtc cgattgagac ttttcaacaa    1320
agggtaatat ccggaaacct cctcggattc cattgcccag ctatctgtca ctttattgtg    1380
aagatagtgg aaaaggaagg tggctcctac aaatgccatc attgcgataa aggaaaggcc    1440
atcgttgaag atgcctctgc cgacagtggt cccaaagatg acccccacc cacgaggagc    1500 atcgtggaaa agaagacgt tccaaccacg tcttcaaagc aagtggattg atgtgatggt    1560
ccgattgaga cttttcaaca aagggtaata tccggaaacc tcctcggatt ccattgccca    1620
gctatctgtc actttattgt gaagatagtg aaaaggaag tggctcctac aaatgccat    1680 cattgcgata aggaaaggc atcgttgaa gatgcctctg ccgacagtgg tcccaaagat    1740 ggaccccac ccacgaggag catcgtgaa aagaagacgt tccaaccac gtcttcaaag    1800 caagtggatt gatgtgatat ctccactgac gtaagggatg acgcacaatc ccactatcct    1860
tcgcaagacc cttcctctat ataaggaagt tcatttcatt tggagaggac acgctgacaa    1920
gctgactcta gcagatctac cgtcttcggt acgcgctcac tccgccctct gcctttgtta    1980
ctgccacgtt tctctgaatg ctctcttgtg tggtgattgc tgagagtggt ttagctggat    2040
ctagaattac actctgaaat cgtgttctgc ctgtgctgat tacttgccgt cctttgtagc    2100
agcaaaatat agggacatgg tagtacgaaa cgaagataga acctacacag caatacgaga    2160
aatgtgtaat ttggtgctta gcggtattta tttaagcaca tgttggtgtt atagggcact    2220
tggattcaga agtttgctgt taatttaggc acaggcttca tactacatgg gtcaatagta    2280
tagggattca tattataggc gatactataa taatttgttc gtctgcagag cttattattt    2340
gccaaaatta gatattccta ttctgttttt gtttgtgtgc tgttaaattg ttaacgcctg    2400
aaggaataaa tataaatgac gaaattttga tgtttatctc tgctccttta ttgtgaccat    2460
```

```
aagtcaagat cagatgcact tgttttaaat attgttgtct gaagaaataa gtactgacag    2520
tattttgatg cattgatctg cttgtttgtt gtaacaaaat ttaaaaataa agagtttcct    2580
ttttgttgct ctccttacct cctgatggta tctagtatct accaactgac actatattgc    2640
ttctctttac atacgtatct tgctcgatgc cttctcccta gtgttgacca gtgttactca    2700
catagtcttt gctcatttca ttgtaatgca gataccaagc ggcctctaga ggatccagga    2760
gcaaccatgg cgcaagttag cagaatctgc aatggtgtgc agaacccatc tcttatctcc    2820
aatctctcga atccagtca acgcaaatct cccttatcgg tttctctgaa gacgcagcag    2880
catccacgag cttatccgat ttcgtcgtcg tggggattga agaagagtgg gatgacgtta    2940
attggctctg agcttcgtcc tcttaaggtc atgtcttctg tttccacggc gtgcatgcta    3000
cacggtgcaa gcagccggcc ggcaaccgct cgcaaatctt ccggcctttc gggaacggtc    3060
aggattccgg gcgataagtc catatcccac cggtcgttca tgttcggcgg tcttgccagc    3120
ggtgagacgc gcatcacggg cctgcttgaa ggtgaggacg tgatcaatac cgggaaggcc    3180
atgcaggcta tgggagcgcg tatccgcaag gaaggtgaca catggatcat tgacggcgtt    3240
gggaatggcg gtctgctcgc ccctgaggcc cctctcgact tcggcaatgc ggcgacgggc    3300
tgcaggctca ctatgggact ggtcggggtg tacgacttcg atagcacgtt catcggagac    3360
gcctcgctca caaagcgccc aatgggccgc gttctgaacc cgttgcgcga gatgggcgta    3420
caggtcaaat ccgaggatgg tgaccgtttg cccgttacgc tgcgcgggcc gaagacgcct    3480
accccgatta cctaccgcgt gccaatggca tccgcccagg tcaagtcagc cgtgctcctc    3540
gccggactga acactccggg catcaccacg gtgatcgagc ccatcatgac cagggatcat    3600
accgaaaaga tgcttcaggg gtttggcgcc aacctgacgg tcgagacgga cgctgacggc    3660
gtcaggacca tccgccttga gggcaggggt aaactgactg gccaagtcat cgatgttccg    3720
ggagacccgt cgtccacggc cttcccgttg gttgcggcgc tgctcgtgcc ggggagtgac    3780
gtgaccatcc tgaacgtcct catgaacccg accaggaccg gcctgatcct cacgcttcag    3840
gagatgggag ccgacatcga ggtgatcaac ccgcgcctgg caggcggtga agacgttgcg    3900
gatctgcgcg tgcgctcctc taccctgaag ggcgtgacgg tcccggaaga tcgcgcgccg    3960
tccatgatag acgagtatcc tattctggcc gtcgccgctg cgttcgccga aggggccacg    4020
gtcatgaacg tcttgagga actccgcgtg aaggaatcgg atcgcctgtc ggcggtggcc    4080
aatggcctga agctcaacgg tgttgactgc gacgagggtg agacctcact cgtggtccgt    4140
ggccggcctg atggcaaggg cctcggcaac gccagtggag cggccgtcgc cacgcacctc    4200
gatcatcgca tcgcgatgtc cttcttggtg atgggtctcg tctcagagaa cccggtgacc    4260
gtcgatgacg ccacgatgat agcgacgagc ttcccagagt tcatggatct gatggcgggc    4320
ctcggggcca agatcgaact gtctgacacg aaggccgctt gaattcccga tcgttcaaac    4380
atttggcaat aaagtttctt aagattgaat cctgttgccg gtcttgcgat gattatcata    4440
taatttctgt tgaattacgt taagcatgta ataattaaca tgtaatgcat gacgttattt    4500
atgagatggg ttttttatgat tagagtcccg caattataca tttaatacgc gatagaaaac    4560
aaaatatagc gcgcaaacta ggataaatta tcgcgcgcgg tgtcatctat gttactagat    4620
cggggatatc cccagcttga tggggatcag attgtcgttt cccgccttca gtttaaacta    4680
tcagcttgtt ggaagttaca tgcaagttgc aacgcggcag ccgccagcgg cgcggagcga    4740
cgaaacgaaa cgtgcgcgcg gctggtccta gagggcggt tgcaacttgc atgtaacttc    4800
cacgcgaccg caggcgtgcg tgcgtcacga ctcgcgtcgt agcctctcgt cactcgcgtt    4860
```

-continued

```
cggcttccgc tcgggggcgc gaatcttctc gacccatcga ggcaagaaac ccaagcctaa    4920
tccgacccgc catggctttc cttgcttgct cccccccccc ttatcttccc gcgggtagta    4980
tataatcatc ccctccgccg ggctcgcttc cttgcgcaac catccaatcc aatcgaacca    5040
ccagtccacc acctgattga ctagagcaaa agcacaagcc gcccacgcat ctcgattgca    5100
gcagcagcag cagcagcaga agcggcgcgc agagctcgtg acgagagcaa ccttccttcc    5160
gttcctcgat cgccatggac aaggtgctag ccttctcgat cctgagcgcg tcgccggccg    5220
acctctcctc cgcgggcgcc ggcttcggcg ggagctgggc gcggctgtcg tggcggaggg    5280
gcgcggacga ccagcgtgcg ccgcggcggg agcagcagca gcggcaggag gaggaggaca    5340
gggagaagcg agaccgcgc tcccgcgacg gcggcgcgca cgcgagcgga gggggagcgg     5400
cggcggcgcc gccgccaccg cggttcgcgc cggagtttga cgggatcgac tggttcggaa    5460
ccatcgtgtc gcgctgatca acaatccggg ctcggccgac gcgccccccg agttaaccac    5520
gtgaccaatc ctgtctactg gagtatgttt tttacctgat ggtggattaa ttgtcccaac    5580
acagataatt gggactccgc gtgttgtaca tacagggaac tgctcactta tcaggggggg    5640
atggggaaca tttatttgtt cctgtcctct gcattttttt tcctgtaccg aaatggatgg    5700
atggtctcca attcgaaacc gagtcctgca gctccaggta atctgccggt ggatgaaccc    5760
aagccgaact gtcccg                                                   5776
```

<210> SEQ ID NO 11
<211> LENGTH: 17
<212> TYPE: DNA
<213> ORGANISM: Artificial Sequence
<220> FEATURE:
<223> OTHER INFORMATION: Chemically Synthesized Oligonucleotide PCR Primer

<400> SEQUENCE: 11
ggcaaccgct cgcaaat                                                  17

<210> SEQ ID NO 12
<211> LENGTH: 17
<212> TYPE: DNA
<213> ORGANISM: Artificial Sequence
<220> FEATURE:
<223> OTHER INFORMATION: Chemically Synthesized Oligonucleotide PCR Primer

<400> SEQUENCE: 12
atcgcccgga atcctga                                                  17

<210> SEQ ID NO 13
<211> LENGTH: 17
<212> TYPE: DNA
<213> ORGANISM: Artificial Sequence
<220> FEATURE:
<223> OTHER INFORMATION: Chemically Synthesized Oligonucleotide PCR Primer

<400> SEQUENCE: 13
ttccggcctt tcgggaa                                                  17

<210> SEQ ID NO 14
<211> LENGTH: 16
<212> TYPE: DNA
<213> ORGANISM: Artificial Sequence
<220> FEATURE:
<223> OTHER INFORMATION: Chemically Synthesized Oligonucleotide PCR Primer

```
<400> SEQUENCE: 14
gcctgccgca gaccaa                                                    16

<210> SEQ ID NO 15
<211> LENGTH: 22
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 15
caatgcagag ctcagcttca tc                                             22

<210> SEQ ID NO 16
<211> LENGTH: 26
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 16
tccagtacgt gcagtccctc ctccct                                         26

<210> SEQ ID NO 17
<211> LENGTH: 17
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 17
cggaaacggt cgggtca                                                   17

<210> SEQ ID NO 18
<211> LENGTH: 27
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 18
ctccatattg accatcatac tcattgc                                        27

<210> SEQ ID NO 19
<211> LENGTH: 21
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 19
aatgtagaaa atcgggacaa t                                              21
```

TRANSGENIC MAIZE EVENT MON 87427 AND THE RELATIVE DEVELOPMENT SCALE

CROSS REFERENCE TO RELATED APPLICATIONS

This application claims the benefit of U.S. Provisional Application No. 61/263,526 filed Nov. 23, 2009, which is hereby incorporated by reference in its entirety herein, and U.S. Provisional Application No. 61/263,530 filed Nov. 23, 2009, which is hereby incorporated by reference in its entirety herein.

INCORPORATION OF SEQUENCE LISTING

The sequence listing that is contained in the file named "56887-0001_seqlisting.txt", which is 19.6 kilobytes (size as measured in Microsoft Windows®) and was created on Nov. 12, 2010, is filed herewith by electronic submission and is hereby incorporated by reference in its entirety herein.

FIELD OF THE INVENTION

The invention relates to the fields of plant breeding, research, and agriculture. More specifically, it relates to transgenic maize event MON 87427 and the nucleotide molecules, plants, plant parts, seeds, cells, agricultural products, and methods related to transgenic maize event MON 87427. It also relates to predicting maize tassel development and utilizing this in the methods of plant breeding, research, and agriculture and the maize hybrid seed produced thereby.

BACKGROUND OF THE INVENTION

Crops having new, desirable traits are useful for plant breeding, research, and agricultural purposes. Such crops may be produced using the methods of biotechnology. However, the production and selection of a commercially suitable transgenic event may require extensive research, analysis, and characterization of a large number of individual plant transformation events in order to select an event having both the desirable trait and the optimal phenotypic and agricultural characteristics necessary to make it suitable for commercial and agricultural purposes. This process of event selection often requires greenhouse and field trials with many events over multiple years, in multiple locations, and under a variety of conditions so that a significant amount of agronomic, phenotypic, and molecular data may be collected. The resulting data and observations must then be analyzed by teams of scientists and agronomists with the goal of selecting a commercially suitable event. The invention provides such a commercially suitable event resulting in a new, desirable trait in maize.

Accurate determination of maize reproductive maturity is also useful for plant breeding, research, and agricultural purposes, such as in maize hybrid seed production. Tools commonly used in the art for predicting and estimating stages of maize growth and development include scales such as V-Stages, which are based on vegetative characteristics, and Growing Degree Units, which are based on the number of growing degree days. However, both of these tools produce estimates of tassel development stage that vary significantly across maize genotypes. Relying on these measurements may thus create a risk of missing the optimally efficacious time for treatment regimens in which development stage is an important factor. The invention provides a Relative Development Scale based on tassel development reconciled across genotypes, which is useful for monitoring and predicting tassel development in maize across various genotypes.

SUMMARY OF THE INVENTION

The invention provides a recombinant DNA molecule comprising a nucleic acid molecule comprising a nucleotide sequence selected from the group consisting of SEQ ID NO: 1-8. The invention also provides a recombinant DNA molecule formed by the junction of an inserted heterologous nucleic acid molecule and genomic DNA of a maize plant, plant cell, or seed. The invention also provides a recombinant DNA molecule derived from transgenic maize event MON 87427, a representative sample of seed having been deposited with the American Type Culture Collection (ATCC®) under Accession No. PTA-7899. The invention also provides a recombinant DNA molecule that is an amplicon diagnostic for the presence of DNA derived from transgenic maize event MON 87427. The invention also provides a recombinant DNA molecule that is in a maize plant, plant cell, seed, progeny plant, plant part, or commodity product derived from transgenic maize event MON 87427.

The invention also provides a DNA molecule comprising a nucleic acid molecule having a nucleotide sequence of sufficient length of contiguous nucleotide sequence of SEQ ID NO: 10 to function as a DNA probe that hybridizes under stringent hybridization conditions with a DNA molecule comprising a nucleotide sequence selected from the group consisting of SEQ ID NO: 1-10 and does not hybridize under the stringent hybridization conditions with a DNA molecule not comprising a nucleotide sequence selected from the group consisting of SEQ ID NO: 1-10.

The invention also provides a pair of DNA molecules consisting of a first DNA molecule and a second DNA molecule different from the first DNA molecule, wherein the first and second DNA molecules each comprise a nucleic acid molecule having a nucleotide sequence of sufficient length of contiguous nucleotides of SEQ ID NO: 10 to function as DNA primers when used together in an amplification reaction with DNA derived from event MON 87427 to produce an amplicon diagnostic for transgenic maize event MON 87427 DNA in a sample.

The invention also provides a method of detecting the presence of a DNA molecule derived from MON 87427 in a sample by contacting a sample with the DNA probe, subjecting the sample and the DNA probe to stringent hybridization conditions, and detecting hybridization of the DNA probe to a DNA molecule in the sample, wherein the hybridization of the DNA probe to the DNA molecule indicates the presence of a DNA molecule derived from transgenic maize event MON 87427 in the sample.

The invention also provides a method of detecting the presence of a DNA molecule derived from transgenic maize event MON 87427 in a sample by contacting a sample with the pair of DNA molecules, performing an amplification reaction sufficient to produce a DNA amplicon comprising a sequence selected from the group consisting of SEQ ID NO: 1-10, and detecting the presence of the DNA amplicon in the reaction, wherein the presence of the DNA amplicon in the reaction indicates the presence of a DNA molecule derived from MON 87427 in the sample.

The invention also provides a DNA detection kit comprising at least one DNA molecule comprising a nucleotide sequence of sufficient length of contiguous nucleotide sequence of SEQ ID NO: 10 to function as a DNA primer or probe specific for detecting the presence of DNA derived from transgenic maize event MON 87427, wherein detection of the DNA is diagnostic for the presence of the transgenic maize event MON 87427 DNA in a sample.

The invention also provides a recombinant maize plant, seed, cell, or plant part thereof comprising a nucleic acid molecule having a nucleotide sequence selected from the group consisting of SEQ ID NO: 1-10. The invention also provides a recombinant maize plant, seed, cell, or plant part having tissue-selective tolerance to glyphosate herbicide treatment. The invention also provides a recombinant maize plant, seed, cell, or plant part, the genome of which produces an amplicon comprising a DNA molecule selected from the group consisting of SEQ ID NO: 1-10 when tested in a DNA amplification method.

The invention also provides a maize plant or seed, wherein the maize plant or seed is derived from transgenic maize event MON 87427. The invention also provides a maize plant or seed, wherein the maize plant or seed is a hybrid having at least one parent derived from transgenic maize event MON 87427.

The invention also provides a nonliving plant material comprising a recombinant DNA molecule selected from the group consisting of SEQ ID NO: 1-10.

The invention also provides a microorganism comprising a nucleic acid molecule having a nucleotide sequence selected from the group consisting of SEQ ID NO: 1-10. The invention also provides a microorganism that is a plant cell.

The invention also provides a commodity product produced from transgenic maize event MON 87427 and comprising a nucleic acid molecule having a nucleotide sequence selected from the group consisting of SEQ ID NO: 1-10, wherein detection of a nucleotide sequence in a sample derived from a commodity product is determinative that the commodity product was produced from transgenic maize event MON 87427. The invention also provides a commodity product selected from the group consisting of whole or processed seeds, animal feed, oil, meal, flour, flakes, bran, biomass, and fuel products. The invention also provides a method of producing a commodity product by obtaining a maize plant or part thereof comprising transgenic maize event MON 87427 and producing a maize commodity product from the maize plant or part thereof.

The invention also provides a method for controlling weeds in a field by planting MON 87427 plants in a field and applying an effective dose of glyphosate herbicide to control weeds in the field without injuring the transgenic maize event MON 87427 plants. The invention also provides a method for controlling weeds in a field, wherein the effective dose of glyphosate herbicide is from about 0.1 pound to about 4 pounds per acre.

The invention also provides a method of producing a maize plant that tolerates application of glyphosate herbicide by sexually crossing a transgenic maize event MON 87427 plant comprising a nucleic acid molecule comprising a nucleotide sequence selected from the group consisting of SEQ ID NO: 1-10 with a second maize plant, thereby producing seed, collecting the seed produced from the cross, growing the seed to produce a plurality of progeny plants, treating the progeny plants with glyphosate, and selecting a progeny plant that is tolerant to glyphosate. The invention also provides a method of producing a maize plant that tolerates application of glyphosate herbicide by selfing a transgenic maize event MON 87427 plant comprising a nucleic acid molecule comprising a nucleotide sequence selected from the group consisting of SEQ ID NO: 1-10, thereby producing seed, collecting the seed produced from the selfing, growing the seed to produce a plurality of progeny plants, treating the progeny plants with glyphosate, and selecting a progeny plant that is tolerant to glyphosate.

The invention also provides a method of producing hybrid maize seed by planting transgenic maize event MON 87427 seed in an area, growing a maize plant from the seed, treating the plant with an effective dose of glyphosate herbicide prior to pollen formation to make the plant male sterile without injuring the plant, fertilizing the plant with pollen from a second parent plant, and harvesting seed from the plant, wherein the seed is hybrid maize seed produced by the cross of transgenic maize event MON 87427 plants with a second parent plant. The invention also provides a method of producing hybrid maize seed, wherein the effective dose of glyphosate herbicide is from about 0.1 pound to about 4 pounds per acre. The invention also provides a method of producing hybrid maize seed, further including planting a second parent plant seed in the area and growing a maize plant from the second parent plant. The invention also provides a method of producing hybrid maize seed, wherein the second parent plant is glyphosate tolerant.

The invention also provides a method for predicting the timing of maize tassel development by selecting a range on a Relative Development Scale, wherein the range indicates maturation to a desired tassel development stage. The invention also provides a method for predicting the timing of maize tassel development, wherein the desired tassel development stage is the optimal tassel development stage for reproductive crossing, tassel sterilization, detasseling, and/or administration of a development modulating treatment to a maize plant. The invention also provides a method for predicting the timing of maize tassel development, wherein the specific flower development stage used to construct the Relative Development Scale is at pollen shed for about 50 percent of a population of maize plants and wherein the range is about 0.62 and about 0.75 on the Relative Development Scale. The invention also provides a method for predicting the timing of maize tassel development, further including administering a development modulating treatment to a maize plant at the desired tassel development stage.

The invention also provides a method of producing hybrid maize seed by planting maize seed for a first parent plant in an area, growing the first parent plant from the maize seed, determining the timing of tassel development for the first parent plant by selecting a range that indicates maturation to a desired tassel development stage on a Relative Development Scale, using the determination of the timing of tassel development to timely administer a development modulating treatment to the first parent plant thereby preventing self-fertilization of the first parent plant, administering the development modulating treatment to the first parent plant, fertilizing the first parent plant with pollen from a second parent plant, and harvesting seed from the first parent plant, wherein the seed is hybrid maize seed produced by the cross of the first parent plant with the second parent plant. The invention also provides the hybrid maize seed produced using the method. The invention also provides a method of producing hybrid maize seed, wherein the development modulating treatment is glyphosate and the first parent plant has tissue-selective glyphosate tolerance. The invention also provides a method of producing hybrid maize seed, wherein the first parent plant is a transgenic maize event MON 87427 plant. The invention also provides a method of producing hybrid maize seed, wherein the second parent plant is glyphosate tolerant.

The foregoing and other aspects of the invention will become more apparent from the following detailed description.

BRIEF DESCRIPTION OF THE SEQUENCES

Figure 1:
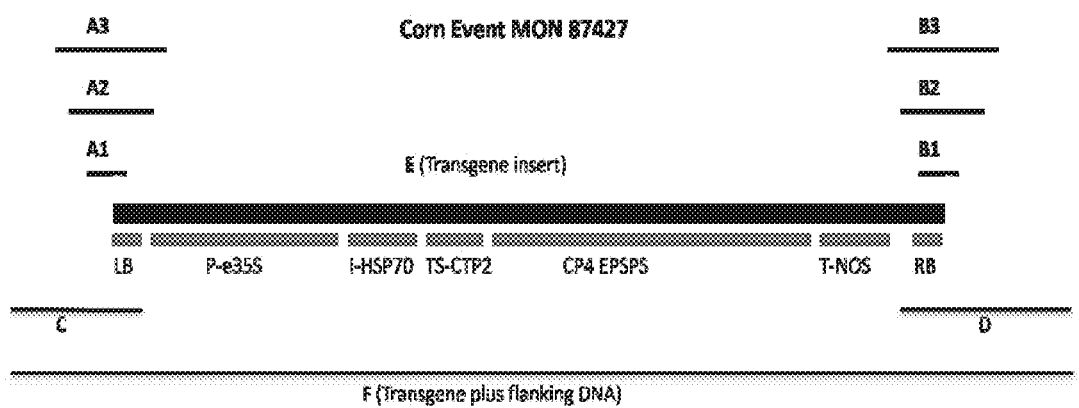
FIG. 1 illustrates the organization of transgenic maize event MON 87427. In the figure, [A1], [A2], and [A3] correspond to the relative position of SEQ ID NO: 1, SEQ ID NO: 3, and SEQ ID NO: 5, respectively, which span the maize genomic DNA flanking the 5' end of the transgene insert and the 5' portion of the transgene insert DNA; [B1], [B2], and [B3] correspond to the relative position of SEQ ID NO: 2, SEQ ID NO: 4, and SEQ ID NO: 6, respectively, which span the maize genomic DNA flanking the 3' end of the transgene insert and the 3' portion of the transgene insert DNA; [C] corresponds to the relative position of SEQ ID NO: 7, which includes the maize genomic DNA flanking the 5' end of the transgene insert and a portion of the 5' end of the transgene insert; [D] corresponds to the relative position of SEQ ID NO: 8, which includes the maize genomic DNA flanking the 3' end of the transgene insert and a portion of the 3' end of the transgene insert; [E] corresponds to the relative position of SEQ ID NO: 9 and the various elements in the transgene insert; and [F] represents the contiguous sequence of MON 87427 provided as SEQ ID NO: 10 and comprising SEQ ID NO: 1-9.

SEQ ID NO: 1 is a twenty nucleotide sequence representing the 5' junction region of a maize genomic DNA and an integrated transgenic expression cassette.

SEQ ID NO: 2 is a twenty nucleotide sequence representing the 3' junction region of a maize genomic DNA and an integrated transgenic expression cassette.

SEQ ID NO: 3 is a sixty nucleotide sequence representing the 5' junction region of a maize genomic DNA and an integrated transgenic expression cassette.

SEQ ID NO: 4 is a sixty nucleotide sequence representing the 3' junction region of a maize genomic DNA and an integrated transgenic expression cassette.

SEQ ID NO: 5 is a one-hundred nucleotide sequence representing the 5' junction region of a maize genomic DNA and an integrated transgenic expression cassette.

SEQ ID NO: 6 is a one-hundred nucleotide sequence representing the 3' junction region of a maize genomic DNA and an integrated transgenic expression cassette.

SEQ ID NO: 7 is the 5' sequence flanking the inserted DNA of MON 87427 up to and including a region of transgene DNA insertion.

SEQ ID NO: 8 is the 3' sequence flanking the inserted DNA of MON 87427 up to and including a region of transgene DNA insertion.

SEQ ID NO: 9 is the sequence fully integrated into the maize genomic DNA and containing the expression cassette DNA.

SEQ ID NO: 10 is the nucleotide sequence representing the contig of the 5' sequence flanking the inserted DNA of MON 87427 (SEQ ID NO: 7), the sequence fully integrated into the maize genomic DNA and containing the expression cassette (SEQ ID NO: 9), and the 3' sequence flanking the inserted DNA of MON 87427 (SEQ ID NO: 8) and includes SEQ ID NO: 1-6.

SEQ ID NO: 11 is transgene-specific assay Event Primer-1 SQ20052 used to identify MON 87427. A PCR amplicon produced from a TAQMAN® (PE Applied Biosystems, Foster City, Calif.) assay using the combination of primers SEQ ID NO: 11 and SEQ ID NO: 12 is a positive result for the presence of the event MON 87427.

SEQ ID NO: 12 is transgene-specific assay Event Primer-1 SQ20053 used to identify MON 87427.

SEQ ID NO: 13 is a transgene-specific assay Event 6-FAM Probe PB10016 used to identify MON 87427. This probe is a 6FAM™-labeled synthetic oligonucleotide. Release of a fluorescent signal in an amplification reaction using primers SEQ ID NO: 11-12 in combination with the 6FAM™-labeled probe is diagnostic of event MON 87427 in a TAQMAN® assay.

SEQ ID NO: 14 is transgene-specific assay Internal Control Primer-1 SQ1241.

SEQ ID NO: 15 is transgene-specific assay Internal Control Primer-1 SQ1242.

SEQ ID NO: 16 is a transgene-specific assay Internal Control VIC Probe PB0084.

SEQ ID NO: 17 is event-specific assay Event Primer-1 SQ12763 used to identify MON 87427. A PCR amplicon produced from a TAQMAN® (PE Applied Biosystems, Foster City, Calif.) assay using the combination of primers SEQ ID NO: 17 and SEQ ID NO: 18 is a positive result for the presence of the event MON 87427.

SEQ ID NO: 18 is event-specific assay Event Primer-1 SQ12886 used to identify MON 87427.

SEQ ID NO: 19 is a transgene-specific assay Event 6-FAM Probe PB4352 used to identify MON 87427.

DETAILED DESCRIPTION

The following definitions and methods are provided to better define the invention and to guide those of ordinary skill in the art in the practice of the invention. Unless otherwise noted, terms are to be understood according to conventional usage by those of ordinary skill in the relevant art.

As used herein, the term "maize" means "corn" or *Zea mays* and includes all plant varieties that can be bred with maize, including wild maize species as well as those plants belonging to *Zea* that permit breeding between species.

"Glyphosate" refers to N-phosphonomethylglycine, which is an herbicide that is an enolpyruvylshikimate 3-phosphate synthase (EPSPS) inhibitor. Glyphosate interferes with the synthesis of aromatic amino acids by inhibiting EPSPS. Glyphosate is commercially available as Roundup® herbicide (Monsanto Company, St. Louis, Mo.).

The invention provides maize transgenic event MON 87427 (also referred to herein as MON 87427). As used herein, the term "event" refers to a product created by the act of inserting a transgenic nucleic acid molecule into the genome of a plant, i.e., by the act of plant transformation to produce a transgenic plant. An "event" is therefore produced by the human acts of: (i) transforming a plant cell in a laboratory with a nucleic acid molecule that includes a transgene of interest, i.e., inserting into the plant cell's genome the nucleic acid construct or molecule, (ii) regenerating a population of transgenic plants resulting from the insertion of the nucleic acid molecule into the genome of the plant, and (iii) selecting a particular plant characterized by the insertion of the nucleic acid molecule into a particular location in the plant's genome. The event may therefore be uniquely and specifically described by a nucleic acid sequence representing at least a portion of the contiguous DNA molecule that was produced in the event by the insertion of the nucleic acid molecule into the particular location in the plant's genome and that includes a portion of the plant's own genomic DNA, which flanks and is physically connected to the inserted DNA molecule, and the inserted nucleic acid molecule. An event is recombinant, produced by human actions, and not found in nontransgenic plants.

The term "event" thus refers to the original transformed plant ("transformant") that includes the nucleic acid molecule inserted into the particular location in the plant's genome. The term "event" also refers to all progeny descended from the transformant that include the nucleic acid molecule inserted into the particular location in the plant's genome. Such progeny are consequently transgenic and comprise the event. Progeny may be produced by any means including self-fertilization, crossing with another plant that comprises the same or different transgene, and/or crossing with a nontransgenic plant, such as one from a different variety. Even after many generations, in any plant referred to as a MON 87427 progeny plant the inserted DNA and the flanking DNA from the original transformed plant will be present and readily identifiable.

The term "event" also refers to the contiguous DNA molecule created in the original transformant (comprising the inserted DNA and the flanking maize genomic DNA immediately adjacent to either side of the inserted DNA) or any DNA molecule comprising that nucleic acid sequence. The contiguous DNA molecule was created by the act of inserting a transgenic nucleic acid molecule into the genome of a plant, i.e., by the act of transformation, and is specific and unique to the particular event. The arrangement of the inserted DNA in MON 87427 in relation to the surrounding maize plant genomic DNA is therefore specific and unique for MON 87427. This DNA molecule is also an integral part of the maize chromosome of MON 87427 and as such is static in the plant and may be inherited by any progeny.

Transgenic maize event MON 87427 plants exhibit commercially acceptable tissue-selective glyphosate tolerance. In MON 87427, the maize vegetative tissues and the maize female reproductive tissues are glyphosate tolerant, but key maize male reproductive tissues critical for maize pollen development are not glyphosate tolerant. Glyphosate-treated MON 87427 plants may therefore be used as a female parent in the production of hybrid seed.

As used herein, the term "recombinant" refers to a non-natural DNA and/or protein and/or an organism that would not normally be found in nature and was created by human intervention, i.e., by human hands. Such human intervention may produce a DNA molecule and/or a plant or seed. As used herein, a "recombinant DNA molecule" is a DNA molecule comprising a combination of DNA molecules that would not naturally occur together and is the result of human intervention, e.g., a DNA molecule that is comprised of a combination of at least two DNA molecules heterologous to each other, and/or a DNA molecule that is artificially synthesized and has a nucleotide sequence that deviates from the nucleotide sequence that would normally exist in nature, and/or a DNA molecule that comprises a nucleic acid molecule artificially incorporated into a host cell's genomic DNA and the associated flanking DNA of the host cell's genome. An example of a recombinant DNA molecule is a DNA molecule comprising at least one sequence selected from SEQ ID NO: 1-10. As used herein, a "recombinant plant" is a plant that would not normally exist in nature, is the result of human intervention, and contains a transgene and/or heterologous DNA molecule incorporated into its genome. As a result of such genomic alteration, the recombinant plant is distinctly different from the related wildtype plant. An example of a recombinant plant is a transgenic maize event MON 87427 plant.

As used herein, the term "transgene" refers to a nucleic acid molecule artificially incorporated into an organism's genome as a result of human intervention. Such transgene may be heterologous to the host cell. The term "transgenic" refers to comprising a transgene, for example a "transgenic plant" refers to a plant comprising a transgene, i.e., a nucleic acid molecule artificially incorporated into the organism's genome as a result of human intervention. As used herein, the term "heterologous" refers to a first molecule not normally found in combination with a second molecule in nature. For example, a molecule may be derived from a first species and inserted into the genome of a second species. The molecule would thus be a heterologous molecule, i.e., heterologous to the organism and artificially incorporated into the organism's genome.

As used herein, the term "chimeric" refers to a single DNA molecule produced by fusing a first DNA molecule to a second DNA molecule, where neither first nor second DNA molecule would normally be found in that configuration, i.e., fused to the other. The chimeric DNA molecule is thus a new DNA molecule not otherwise normally found in nature. An example of a chimeric DNA molecule is a DNA molecule comprising at least one sequence selected from SEQ ID NO: 1-10.

The invention provides DNA molecules and their corresponding nucleotide sequences. As used herein, the term "DNA", "DNA molecule", "nucleic acid molecule" refers to a double-stranded DNA molecule of genomic or synthetic origin, i.e., a polymer of deoxyribonucleotide bases or a nucleotide molecule, read from the 5' (upstream) end to the 3' (downstream) end. As used herein, the term "DNA sequence"

or "nucleotide sequence" refers to the nucleotide sequence of a DNA molecule. The nomenclature used herein is that required by Title 37 of the United States Code of Federal Regulations §1.822 and set forth in the tables in WIPO Standard ST.25 (1998), Appendix 2, Tables 1 and 3. By convention and as used herein, the nucleotide sequences of the invention, such as those provided as SEQ ID NO: 1-10 and fragments thereof, are provided with reference to only one strand of the two complementary nucleotide sequence strands, but by implication the complementary sequences (i.e. the sequences of the complementary strand), also referred to in the art as the reverse complementary sequences, are within the scope of the invention and are expressly intended to be within the scope of the subject matter claimed. Thus, as used herein references to SEQ ID NO: 1-10 and fragments thereof include and refer to the sequence of the complementary strand and fragments thereof.

As used herein, the term "fragment" refers to a portion of or an incomplete smaller piece of a whole. For example, fragments of SEQ ID NO: 10 would include sequences that are at least about 10 nucleotides, at least about 20 nucleotides, or at least about 50 nucleotides of the complete sequence of SEQ ID NO: 10.

The nucleotide sequence corresponding to the complete nucleotide sequence of the inserted transgenic DNA and substantial segments of the maize genome DNA flanking either end of the inserted transgenic DNA is provided herein as SEQ ID NO: 10. A subsection of this is the inserted transgenic DNA (also referred to herein as the transgene insert or the inserted DNA) provided as SEQ ID NO: 9. The nucleotide sequence of the maize genomic DNA physically linked by phosphodiester bond linkage to and therefore flanking the 5' end of the inserted transgenic DNA, and containing 10 nt of the transgene inserted DNA, is set forth as shown in SEQ ID NO: 7. The nucleotide sequence of the maize genome DNA physically linked by phosphodiester bond linkage to and therefore flanking the 3' end of the inserted transgenic DNA, and containing 10 nt of the transgene inserted DNA, is set forth as shown in SEQ ID NO: 8.

The MON 87427 further comprises two regions referred to as junctions. A "junction" is where one end of the inserted transgenic DNA has been inserted into and connected to the genomic DNA. A junction spans, i.e., extends across, a portion of the inserted transgenic DNA and the adjacent flanking genomic DNA and as such comprises the connection point of these two as one contiguous molecule. One junction is at the 5' end of the inserted transgenic DNA and one is at the 3' end of the inserted transgenic DNA, referred to herein as the 5' and 3' junction, respectively. A "junction sequence" or "junction region" refers to the DNA sequence and/or corresponding DNA molecule of the junction. Junction sequences of MON 87427 can be designed by one of skill in the art using SEQ ID NO: 10. Examples of junction sequences of MON 87427 are provided as SEQ ID NO: 1-6. SEQ ID NO: 1 is a 20 nucleotide sequence spanning the junction between the maize genomic DNA and the 5' end of the transgenic insert DNA; SEQ ID NO: 3 is a 60 nucleotide sequence spanning the junction between the maize genomic DNA and the 5' end of the transgenic insert DNA; SEQ ID NO: 5 is a 100 nucleotide sequence spanning the junction between the maize genomic DNA and the 5' end of the transgenic insert DNA. SEQ ID NO: 2 is a 20 nucleotide sequence spanning the junction between the maize genomic DNA and the 3' end of the inserted DNA; SEQ ID NO: 4 is a 60 nucleotide sequence spanning the junction between the maize genomic DNA and the 3' end of the inserted DNA; SEQ ID NO: 6 is a 100 nucleotide sequence spanning the junction between the maize genomic DNA and the 3' end of the inserted DNA. FIG. 1 illustrates the physical arrangement of SEQ ID NO: 1-10 arranged from 5' to 3'. Any segment of DNA derived from transgenic MON 87427 that includes SEQ ID NO: 1-6 is within the scope of the invention. The invention thus provides a DNA molecule that contains at least one of the nucleotide sequences as set forth in SEQ ID NO: 1-6. The junction sequences of event MON 87427 are present as part of the genome of a transgenic maize event MON 87427 plant, seed, or cell. The identification of any one or more of SEQ ID NO: 1-6 in a sample derived from a maize plant, seed, or plant part is determinative that the DNA was obtained MON 87427 and is diagnostic for the presence in a sample of DNA from MON 87427.

The invention provides exemplary DNA molecules that can be used either as primers or probes for diagnosing the presence of DNA derived from maize plant event MON 87427 in a sample. Such primers or probes are specific for a target nucleic acid sequence and as such are useful for the identification of MON 87427 nucleic acid sequences by the methods of the invention described herein.

A "primer" is a nucleic acid molecule that is designed for use in annealing or hybridization methods that involve thermal amplification. A pair of primers may be used with template DNA, such as a sample of maize genomic DNA, in a thermal amplification, such as polymerase chain reaction (PCR), to produce an amplicon, where the amplicon produced from such reaction would have a DNA sequence corresponding to sequence of the template DNA located between the two sites where the primers hybridized to the template. As used herein, an "amplicon" is DNA that has been synthesized using amplification techniques. Amplicons of the invention have a sequence comprising one or more of SEQ ID NO: 1-10 or fragments thereof. A primer is typically designed to hybridize to a complementary target DNA strand to form a hybrid between the primer and the target DNA strand, and the presence of the primer is a point of recognition by a polymerase to begin extension of the primer (i.e., polymerization of additional nucleotides into a lengthening nucleotide molecule) using as a template the target DNA strand. Primer pairs, as used in the invention, are intended to refer to use of two primers binding opposite strands of a double stranded nucleotide segment for the purpose of amplifying linearly the nucleotide segment between the positions targeted for binding by the individual members of the primer pair. Examples of primer sequences are provided as SEQ ID NO: 11-12, SEQ ID NO: 14-15 and SEQ ID NO: 17-18. The primer pair of SEQ ID NO: 14-15 and the primer pair of SEQ ID NO: 17-18 each have a first DNA molecule and a second DNA molecule (that is different from the first DNA molecule) where both molecules are each of sufficient length of contiguous nucleotides to function as DNA primers that, when used together in a DNA amplification reaction with template DNA derived from MON 87427, produce an amplicon diagnostic for the presence in a sample of DNA from MON 87427.

A "probe" is a nucleic acid molecule that is complementary to a strand of a target nucleic acid for use in annealing or hybridization methods. Probes according to the invention include not only deoxyribonucleic or ribonucleic acids but also polyamides and other probe materials that bind specifically to a target DNA sequence and the detection of such binding can be useful in diagnosing, discriminating, determining, or confirming the presence of that target DNA sequence in a particular sample. A probe may be attached to a conventional detectable label or reporter molecule, e.g., a radioactive isotope, ligand, chemiluminescent agent, or enzyme. Examples of sequences useful as probes for detecting MON 87427 are SEQ ID NO: 1-2, SEQ ID NO: 13, SEQ ID NO: 16, SEQ ID NO: 19.

Methods for designing and using primers and probes are well know in the art and are described by, for example, Joseph Sambrook, Molecular Cloning: A Laboratory Manual, Third Edition, Cold Spring Harbor Laboratory Press (2001) and Current Protocols in Molecular Biology, Wiley-Blackwell. DNA molecules comprising fragments of SEQ ID NO: 1-10 and useful as primers and probes for detecting MON 87427 can readily be designed by one of skill in the art for use as probes in hybridization detection methods, e.g., Southern Blot method The DNA molecules and corresponding nucleotide sequences provided herein are therefore useful for, among other things, identifying MON 87427, selecting plant varieties or hybrids comprising MON 87427, detecting the presence of DNA derived from the transgenic MON 87427 in a sample, and monitoring samples for the presence and/or absence of MON 87427 or plant parts derived from MON 87427.

The invention provides maize plants, progeny, seeds, plant cells, plant parts, and commodity products. These plants, progeny, seeds, plant cells, plant parts, and commodity products contain a detectable amount of a nucleotide of the invention, i.e., such as a nucleic acid molecule comprising at least one of the sequences provided as SEQ ID NO: 1-10. Plants, progeny, seeds, plant cells, and plant parts of the invention may also contain one or more additional transgenes. Such transgene may be any nucleotide sequence encoding a protein or RNA molecule conferring a desirable trait including but not limited to increased insect resistance, increased water use efficiency, increased yield performance, increased drought resistance, increased seed quality, improved nutritional quality, and/or increased herbicide tolerance, in which the desirable trait is measured with respect to a maize plant lacking such additional transgene.

The invention provides maize plants, progeny, seeds, plant cells, and plant parts, and leaves derived from a transgenic maize plant event MON 87427. A representative sample of MON 87427 seed has been deposited according to the Budapest Treaty for the purpose of enabling the invention. The repository selected for receiving the deposit is the American Type Culture Collection (ATCC) having an address at 10801 University Boulevard, Manassas, Va. USA, Zip Code 20110. The ATCC repository has assigned the accession No. PTA-7899 to the event MON 87427 seed.

The invention provides a microorganism comprising a DNA molecule having SEQ ID NO: 1-10 present in its genome. An example of such a microorganism is a transgenic plant cell. Microorganisms, such as a plant cell of the invention, are useful in many industrial applications, including but not limited to: (i) use as research tool for scientific inquiry or industrial research; (ii) use in culture for producing endogenous or recombinant carbohydrate, lipid, nucleic acid, or protein products or small molecules that may be used for subsequent scientific research or as industrial products; and (iii) use with modern plant tissue culture techniques to produce transgenic plants or plant tissue cultures that may then be used for agricultural research or production. The production and use of microorganisms such as transgenic plant cells utilizes modern microbiological techniques and human intervention to produce a man-made, unique microorganism. In this process, recombinant DNA is inserted into a plant cell's genome to create a transgenic plant cell that is separate and unique from naturally occurring plant cells. This transgenic plant cell can then be cultured much like bacteria and yeast cells using modern microbiology techniques and may exist in an undifferentiated, unicellular state. The new plant cell's genetic composition and phenotype is a technical effect created by the integration of the heterologous DNA into the genome of the cell. Another aspect of the invention is a method of using a microorganism of the invention. Methods of using microorganisms of the invention, such as transgenic plant cells, include (i) methods of producing transgenic cells by integrating recombinant DNA into genome of the cell and then using this cell to derive additional cells possessing the same heterologous DNA; (ii) methods of culturing cells that contain recombinant DNA using modern microbiology techniques; (iii) methods of producing and purifying endogenous or recombinant carbohydrate, lipid, nucleic acid, or protein products from cultured cells; and (iv) methods of using modern plant tissue culture techniques with transgenic plant cells to produce transgenic plants or transgenic plant tissue cultures.

Plants of the invention may pass along the event DNA, including the transgene insert, to progeny. As used herein, "progeny" includes any plant, seed, plant cell, and/or regenerable plant part comprising the event DNA derived from an ancestor plant and/or a nucleic acid molecule having at least one of the sequences provided as SEQ ID NO: 1-10. Plants, progeny, and seeds may be homozygous or heterozygous for the transgene.

Progeny may be grown from seeds produced by a MON 87427 plant and/or from seeds produced by a plant fertilized with pollen from a MON 87427 plant. Plants of the invention may be produced by self-pollination or cross-pollination and/or may be used in self-pollination or cross-pollination methods. Thus in one embodiment, a MON 87427 plant can be cross-pollinated by a different maize plant to produce hybrid offspring. Breeding methods useful with MON 87427 maize plants are known in the art.

The invention provides a plant part that is derived from MON 87427. As used herein, a "plant part" refers to any part of a plant which is comprised of material derived from a MON 87427 plant. Plant parts include but are not limited to pollen, ovule, pod, flower, root or stem tissue, fibers, and leaves. Plant parts may be viable, nonviable, regenerable, and/or nonregenerable.

The invention provides a commodity product that is produced from transgenic maize event MON 87427 and comprises a nucleic acid molecule having a nucleotide sequence selected from the group consisting of SEQ ID NO: 1-10. As used herein, a "commodity product" refers to any composition or product which is comprised of material derived from a MON 87427 plant, seed, plant cell, or plant part. Commodity products may be viable or nonviable. Nonviable commodity products include but are not limited to nonviable seeds and grains; processed seeds, seed parts, and plant parts; dehydrated plant tissue, frozen plant tissue, and processed plant tissue; seeds and plant parts processed for animal feed for terrestrial and/or aquatic animals consumption, oil, meal, flour, flakes, bran, fiber, milk, cheese, paper, cream, wine, and any other food for human consumption; and biomasses and fuel products. Viable commodity products include but are not limited to seeds and plant cells. Transgenic maize event MON 87427 can thus be used to manufacture any commodity product typically acquired from maize. A commodity product that is derived from the MON 87427 may contain a detectable amount of the specific and unique DNA corresponding to MON 87427, and specifically may contain a detectable amount of a nucleic acid molecule having at least one of the sequences provided as SEQ ID NO: 1-10. Detection of one or more of these sequences in a sample of a commodity product derived from, made up of, consisting of, or comprising a corn plant, a corn seed, a corn plant cell, or a corn plant part is conclusive and determinative of the presence of biological material derived from corn event MON87427 in such commodity product, and the detection of such a nucleic acid molecule may be used for determining the content and/or the source of the commodity product. Any standard method of detection for nucleic acid molecules may be used, including methods of detection disclosed herein.

The plants, progeny, seeds, plant cells, plant parts, and commodity products of the invention are therefore useful for, among other things, growing plants for the purpose of producing seed and/or plant parts of MON 87427 for agricultural purposes, producing progeny of MON 87427 for plant breeding and research purposes, use with microbiological techniques for industrial and research applications, and sale to consumers.

The invention provides methods for controlling weeds using glyphosate herbicide and MON 87427. A method for controlling weeds in a field is provided and consists of planting MON 87427 varietal or hybrid plants in a field and applying an herbicidally effective dose of glyphosate to the field for the purpose of controlling weeds in the field without injuring the MON 87427 plants. Such application of glyphosate herbicide may be pre-emergence, i.e., any time after MON 87427 seed is planted and before MON 87427 plants emerge, or post-emergence, i.e., any time after MON 87427 plants emerge. An herbicidally effective dose of glyphosate for use in the field for controlling weeds should consist of a range from about 0.1 pound per acre to as much as about 4 pounds of glyphosate per acre over a growing season. Multiple applications of glyphosate may be used over a growing season, for example, two applications (such as a pre-planting application and a post-emergence application or a pre-emergence application and a post-emergence application) or three applications (such as a pre-planting application, a pre-emergence application, and a post-emergence application).

Methods for producing an herbicide tolerant transgenic maize event MON 87427 plant are provided. Progeny produced by these methods may be varietal or hybrid plants; may be grown from seeds produced by a MON 87427 plant and/or from seeds produced by a plant fertilized with pollen from a MON 87427 plant; and may be homozygous or heterozygous for the transgene. Progeny may be subsequently self-pollinated or cross-pollinated.

A maize plant that tolerates application of glyphosate herbicide may be produced by sexually crossing a MON 87427 plant comprising a nucleic acid molecule comprising at least one of the sequences provided as SEQ ID NO: 1-10 with another maize plant and thereby producing seed, which is then collected and grown into progeny plants. These progeny may then be treated with glyphosate herbicide and progeny that are tolerant to glyphosate herbicide may be selected. Alternatively, these progeny plants may be analyzed using diagnostic methods to select for progeny plants that contain MON 87427 DNA.

In practicing the methods of the invention, the step of sexually crossing one plant with another plant, i.e., cross-pollinating may be accomplished or facilitated by human intervention, for example: by human hands collecting the pollen of one plant and contacting this pollen with the style or stigma of a second plant and then optionally preventing further fertilization of the fertilized plant; by human hands and/or actions removing (e.g., by detasseling), destroying (e.g., by use of chemical agents), or covering the stamen or anthers of a plant so that natural self-pollination is prevented and cross-pollination would have to take place in order for fertilization to occur; by human placement of pollinating insects in a position for "directed pollination" (e.g., by placing beehives in orchards or fields or by caging plants with pollinating insects); by human opening or removing of parts of the flower to allow for placement or contact of foreign pollen on the style or stigma (e.g., in maize which naturally has flowers that hinder or prevent cross-pollination, making them naturally obligate self-pollinators without human intervention); by selective placement of plants in a specific area (e.g., intentionally planting plants in pollinating proximity); and/or by application of chemicals to precipitate flowering or to foster receptivity (of the stigma for pollen).

In practicing the methods of the invention, the step of sexually fertilizing a maize plant by self-pollination, i.e., selfing, may be accomplished or facilitated by human intervention, for example: by human hands collecting the pollen of a plant and contacting this pollen with the style or stigma of the same plant and then optionally preventing further fertilization of the fertilized plant; by human hands and/or actions removing (e.g., by detasseling), destroying (e.g., by use of chemical agents), or covering the stamen or anthers of a plant so that natural self-pollination is prevented and manual self-pollination would have to take place in order for fertilization to occur; by human placement of pollinating insects in a position for "directed pollination" (e.g., by caging a plant alone with pollinating insects); by human manipulation of a plant's reproductive parts to allow for or enhance self-pollination; by selective placement of plants (e.g., intentionally planting other plants beyond pollinating proximity); and/or by application of chemicals to precipitate flowering or to foster receptivity (of the stigma for pollen).

The invention provides plants and methods useful in hybrid maize seed production.

The maize plant has separate male and female flowering parts. The tassel is the male structure and the ear shoot is the female flowering structure of the plant. The flowering stage in maize involves pollen shed and silking. Maize pollen may fertilize the same plant (self-pollination) or a different plant (cross-pollination). If the male structures of the plant are not removed prior to pollen shed, then the maize plant will self-pollinate to some extent. For hybrid seed production, the female structures of a first maize plant are cross-pollinated with the pollen from a second maize plant. Efficient hybrid seed production thus requires that a plant's own pollen not be permitted to self-fertilize the plant. Methods to enhance hybrid maize seed production provided herein comprise growing in an area a seed or plant comprising MON 87427 and one or more other maize plant(s). The event MON 87427 plants are then treated with glyphosate prior to pollen formation, thereby making the event MON 87427 plants male sterile and incapable of self-fertilization. The event MON 87427 plants are then pollinated by pollen from the other maize plant(s) using any of the methods described herein. The other maize plant(s) may or may not be glyphosate tolerant. Maize seed is then harvested from the event MON 87427 plants, wherein the seed harvested from the treated MON 87427 plants has a higher yield of hybrid maize seed (i.e. higher percentage of hybrid seed harvested or higher hybrid seed purity) than maize seed harvested from untreated event MON 87427 plants or from other maize plant(s) under the same conditions. The maize seed harvested from untreated event MON 87427 plants under the same conditions would have a higher percentage of non-hybrid seed (i.e., inbred seed produced by self-pollination) and thus a lower yield of hybrid maize seed.

The plants and methods of the invention may also be used for maize breeding purposes with methods known in the art including using the methods described in U.S. Pat. No. 7,314,970, which is hereby incorporated by reference herein, and U.S. Patent Publication No. 20090165166, which is hereby incorporated by reference herein.

Plants, progeny, and seeds encompassed by these methods and produced by using these methods will be distinct from other maize plants. For example the MON 87427 plants, progeny, and seeds of the invention are transgenic and recombinant and as such created by human intervention and contain a detectable amount of a nucleic acid molecule having at least one of the sequences provided as SEQ ID NO: 1-10.

The methods of the invention are therefore useful for, among other things, controlling weeds in a field while growing plants for the purpose of producing seed and/or plant parts of MON 87427 for agricultural or research purposes, selecting for progeny of MON 87427 for plant breeding or research purposes, and producing progeny plants and seeds of MON 87427.

The plants, progeny, seeds, plant cells, plant parts, and commodity products of the invention may be evaluated for DNA composition, gene expression, and/or protein expression. Such evaluation may be done by using standard methods such as PCR, northern blotting, southern analysis, western blotting, immuno-precipitation, and ELISA or by using the methods of detection and/or the detection kits provided herein.

Methods of detecting the presence of materials specific to MON 87427 in a sample are provided. It is possible to detect the presence of a nucleic acid molecule of the invention by using the probes and primers of the invention with any nucleic acid detection method used in the art, such as polymerase chain reaction (PCR) or DNA hybridization. One method provides for contacting a DNA sample with a primer pair that is capable of producing an amplicon from event MON 87427 DNA, performing an amplification reaction and thereby producing a DNA amplicon comprising at least one of the nucleotide sequences provided as SEQ ID NO: 1-10, and then detecting the presence or absence of the amplicon molecule and optionally confirming within the sequence of the amplicon a sequence comprising to at least one of the sequences provided as SEQ ID NO: 1-10. The presence of such an amplicon is determinative and/or diagnostic for the presence of the MON 87427 specific DNA and thus MON 87427 biological material in the sample. Another method provides for contacting a DNA sample with a DNA probe, subjecting the probe and the DNA sample to stringent hybridization conditions, and then detecting hybridization between the probe and the target DNA sample. Detection of hybridization is diagnostic for the presence of MON 87427 specific DNA in the DNA sample. Nucleic-acid amplification, nucleic acid hybridization, and DNA sequencing can be accomplished by any of the methods known in the art. One exemplary technique useful in practicing this invention is TAQMAN® (PE Applied Biosystems, Foster City, Calif.).

The sequence of the heterologous DNA insert, junction sequences, or flanking sequences from MON 87427 (with representative seed samples deposited as ATCC PTA-7899) can be verified (and corrected if necessary) by amplifying such sequences from the event using primers derived from the sequences provided herein followed by standard DNA sequencing of the amplicon or of the cloned DNA.

DNA detection kits are provided. Variations on such kits can also be developed using the compositions and methods disclosed herein and the methods well known in the art of DNA detection. DNA detection kits are useful for the identification of MON 87427 DNA in a sample and can be applied to methods for breeding maize plants containing MON 87427 DNA. The kits may contain DNA primers or probes that are similar or complementary to SEQ ID NO: 1-10 or fragments thereof.

The kits and detection methods of the invention are therefore useful for, among other things, identifying MON 87427, selecting plant varieties or hybrids comprising MON 87427, detecting the presence of DNA derived from the transgenic MON 87427 in a sample, and monitoring samples for the presence and/or absence of MON 87427 or plant parts derived from MON 87427.

Figure 3:
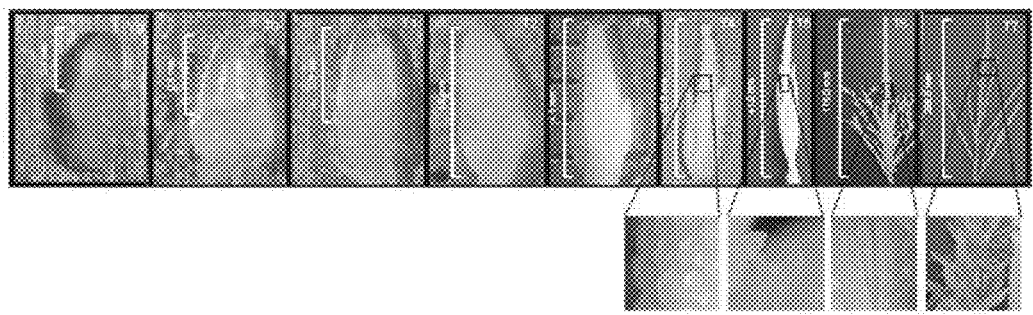
FIG. 3 illustrates tassel development stages used in constructing the Relative Development Scale. Approximate size is shown between brackets. In the figure, Vg is meristem at vegetative stage; T0 is switch from vegetative to reproductive; T1 is reproductive growing point visible (0.9 mm); T2 is lateral branch primordia visible (1.8 mm); T3 is spikelet primordia visible (4.1 mm); T4 is central axis and lateral axis elongation (12.9 mm); T5 is beginning of anthers differentiation (41.0 mm); T6 is beginning of pollen differentiation (175 mm); and T7 is anther exertion and pollen shed (285.0 mm).

The invention provides a Relative Development Scale useful for monitoring and/or determining reproductive development in maize. This novel Relative Development Scale resolves the developmental and reproductive maturation differences across various maize varieties and inbreds by providing a time scale that expresses tassel development stages relative to flowering. The Relative Development Scale diminishes the observed differences in tassel development and tassel growth across genotypes. Tassel development in the various stages of maturation is illustrated in FIG. 3.

Maize development is often determined by a scale of stages based on vegetative events, commonly known as V-Stages. These stages are defined according to the uppermost leaf in which the leaf collar is visible. VE corresponds to emergence, V1 corresponds to first leaf, V2 corresponds to second leaf, V3 corresponds to third leaf, V(n) corresponds to nth leaf. VT occurs when the last branch of tassel is visible but before silks emerge. When staging a field of maize, each specific V-stage is defined only when 50 percent or more of the plants in the field are in or beyond that stage. However, the use of this vegetative scale to determine reproductive maturity may be complicated by the fact that vegetative development does not necessarily correlate to reproductive development across all genotypes. In addition, not all inbreds differentiate the same number of leaves, field inspectors are not always consistent in their assessment, and the first leaves to differentiate start to senesce fairly early in the season so if leaves are not properly marked during the early stages it becomes very difficult to properly identify the V-stages later on.

Another common tool for predicting and estimating stages of maize growth and development is Growing Degree Units (GDU). A factor in the growth and development of maize is heat. Heat is typically measured at a single point in time and is expressed as temperature, but it can also be measured over a period of time and be expressed as heat units. These heat units are commonly referred to as GDU's. GDU's may be defined as the difference between the average daily temperature and a selected base temperature subject to certain restrictions. GDU's are calculated using the following equation:

$$\text{Growing Degree Unit} = \{(H+L)/2\} - B$$

where H is the daily high (but no higher than 86° F.), L is the daily low (but no lower than 50° F.), and B is the base of 50° F. Because maize growth is minor when temperatures are greater than 86° F. or less than 50° F., limits are set on the daily high and low temperatures used in the formula. The lower cutoff for daily temperature also prevents calculation of negative values. Therefore, if the daily high temperature exceeds 86° F., the daily high temperature used in the GDU formula would be set at 86° F. Conversely, if the daily low temperature drops below 50° F., the daily low temperature used in the GDU formula would be set at 50° F. If the daily high temperature does not exceed 50° F., then no GDU is recorded for that day. The maximum GDU a maize plant can accumulate in a day is 36, the minimum is zero. A maize plant's maturity rating is identified by the sum of the daily GDU values over a specified amount of time. The time period that most maize seed producers use is from the point of planting to physiological maturity or the point at which grain fill is virtually complete. In most U.S. states, accumulated GDU's are kept for most geographic areas and are available from the USDA Crop Reporting Service or the State Extension Services. Additionally, an instrument for obtaining GDU information at a particular location is also described in U.S. Pat. No. 6,967,656, which is hereby incorporated by reference in its entirety herein. As with V-Stages, GDU measurements may vary significantly relative to tassel development stage across genotypes and may not be a reliable predictor of tassel development.

As used herein, a "Relative Development Scale" is defined as a scale created by dividing the GDU at a given tassel development stage by the GDU required to achieve a particular stage of pollen shed. A regression line is then constructed with this information for each genotype or inbred variety. A Relative Development Scale may be constructed using the methods described herein and is based on the correlation between the GDU requirements necessary to reach a certain maize flower development stage relative to a given tassel development stage. As such, a Relative Development Scale is useful for predicting tassel development in maize across various genotypes and inbred varieties and may be used as an alternative to using V-Stages or GDU's in plant breeding and agricultural methods.

As used herein, "flower development stage" is defined according to the extent to which a population of plants is shedding pollen, referred to as P-Stage. Flower development stage is expressed as Px, where P stands for "pollen" and "x" indicates the percentage of plants within a population that are shedding pollen. The Relative Development Scale of the invention is based on a regression derived by dividing GDUs at a given tassel development stage by the number of GDUs required to achieve a particular stage of pollen shed. This is expressed as follows:

Relative Development Scale=(GDU to $Tn$/GDU to $Px$)

where "GDU to Tn" is the amount of GDU (growing degree units) required to a reach a certain tassel development stage where n could range from 0 to 7, and where "GDU to Px" is the amount of GDU required to reach a certain flower development stage or P-Stage where x can range from 0 to 100 (an example of this is P50 defined as 50% of the plants in the field have started shedding pollen).

Figure 5:
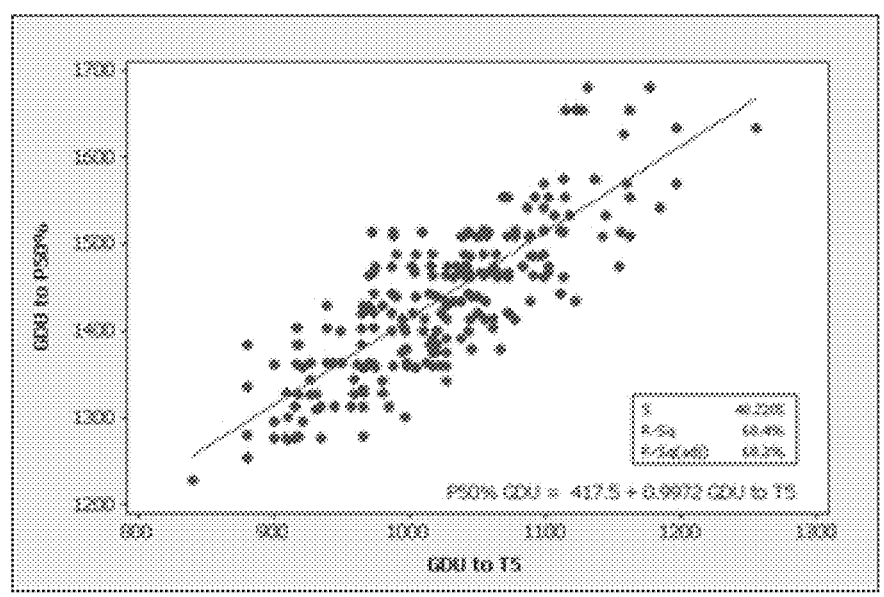
FIG. 5 illustrates the correlation between GDU requirements for T5-Stage and those to P50% and more specifically shows the regression line produced using the correlation between GDU requirements to T5 and to P50%. Each dot represents a different inbred, averaged across locations.

The regression may be based on the correlative relationship between any tassel development stage and flower development stage or P-Stage GDU requirements. Such correlative relationship is expressed by dividing the GDU required to reach a specified tassel development stage by the GDU required to reach a specified flower development stage or P-Stage. In one embodiment of the invention, the flower development stage or P-Stage for the regression is P50, wherein 50% of a population of the maize plants is shedding pollen. In another embodiment, the flower development stage or P-Stage of pollen shed for calculating the regression may be from about 1% to 100%, including about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, and 99%. The tassel development stage for the regression may be between T0 and T7, such as T0, T1, T2, T3, T4, T5, T6, and T7. Regardless of tassel development stage and flower development stage chosen for creating the regression, a Relative Development Scale may be derived by plotting the relationship of GDUs required to achieve a particular stage of pollen shed relative to the number of GDUs required to achieve a given tassel development stage. This aspect is illustrated in FIG. 5.

As used herein, the term "determining" refers to the act of measuring, assessing, evaluating, estimating, monitoring, and/or predicting. For example, "determining tassel development" as used herein includes measuring the current stage of tassel development, monitoring the progression of tassel development, and/or predicting the occurrence of a future stage of tassel development.

The invention therefore provides a method for producing a Relative Development Scale comprising measuring the Growing Degree Units required for a population of maize plants to mature to a specific tassel development stage; measuring the Growing Degree Units required for said population of maize plants to mature to a specific flower development stage; and creating a regression line by dividing said measured Growing Degree Units required for said population of maize plants to mature to said specified tassel development stage by said measured Growing Degree Units required for said population of maize plants to mature to said specified flower development stage. The measuring step may be repeated for at least two populations of maize plants. The measuring step may be repeated for multiple tassel development stages and/or multiple flower development stages. The specific flower development stage may be pollen shed for about 50 percent of the population of maize plants.

The invention also provides a method for determining the optimal range within the Relative Development Scale for a treatment regimen linked to tassel development, thus allowing one to determine the optimal timing of a treatment regimen in which development stage is an important factor. An example of this is the application of a single common chemical agent treatment schedule for maximum efficacy in causing maize tassel sterility across diverse parent genotypes in the production of hybrid maize seed, regardless of genotype or maturity group.

As used herein, the term "hybrid seed" is seed produced by cross-pollinating two plants. Plants grown from hybrid seed may have improved agricultural characteristics, such as better yield, greater uniformity, and/or disease resistance. Hybrid seed does not breed true, i.e., the seed produced by self-fertilizing a hybrid plant (the plant grown from a hybrid seed) does not reliably result the next generation in an identical hybrid plant. Therefore, new hybrid seed must be produced from the parent plant lines for each planting. Since most crop plants have both male and female organs, hybrid seed can only be produced by preventing self-pollination of the female parent and allowing or facilitating pollination with the desired pollen. There are a variety of methods to prevent self-pollination of the female parent, one method by which self-pollination is prevented is mechanical removal of the pollen producing organ before pollen shed. Commercial hybrid maize seed (maize, *Zea mays*) production typically involves planting the desired male and female parental lines, usually in separate rows or blocks in an isolated field, treating the female parent plant to prevent pollen shed, ensuring pollination of the female by only the designated male parent, and harvesting hybrid seed from only the female parent. Hybrid seed may be the result of a single cross (e.g., a first generation cross between two inbred lines), a modified single cross (e.g., a first generation cross between two inbred lines, one or other of which may have been modified slightly by the use of closely related crossing), a double cross (e.g., a first generation of a cross between two single crosses), a three-way cross (e.g., a first generation of a cross between a single cross and an inbred line), a top cross (e.g., the first generation of a cross between an inbred line and an open-pollinated variety, or the first generation of a cross between a single-cross and an open-pollinated variety), or an open pollinated variety (e.g., a population of plants selected to a standard which may show variation but has characteristics by which a variety can be differentiated from other varieties).

In hybrid seed production, pollen production and/or shed may be prevented in a female parent plant in order to facilitate pollination of the female by only the designated male parent and thus produce hybrid seed. Such prevention may be achieved by any method or means known to those of skill in the art, including but not limited to, manual or hand detasseling, mechanical detasseling, use of a genetic means of pollination control, and/or use of a chemical agent. Any of these may be combined or used individually. Detasseling may be done manually or by hand and is typically performed by a person removing the tassels from a maize plant, usually by pulling the tassel off. Mechanical or machine detasseling typically utilizes a detasseling machine called a "cutter" that moves through rows of maize and cuts off the top portion of the plant. A "puller" machine then moves through the maize rows a few days later and pulls the tassel out of the plant by catching it between two rollers moving at a high speed. Mechanical detasselers useful in practicing the methods of the invention include those mounted on high clearance machines. The cutter may be a rotating blade or knife that operates at various planes from horizontal to vertical, adjustable in height, to cut or shred the top of the maize plant including the tassel. The puller may be two small wheels or rollers, adjustable in height, that rotate in opposite directions and grasp the tassel and upper leaves, pulling them upward in a manner comparable to a hand detasseling operation. Pullers and cutters may be used separately or together and/or in combination with other detasseling methods. The window of time for detasseling is usually the most critical and difficult to manage period in hybrid maize seed production. In the art, chemical agents and/or genetic means are also used to prevent viable pollen formation or pollen shed.

The invention provides a method for determining the timing of tassel development by selecting a range on a Relative Development Scale, wherein the selected range indicates maturation to a desired tassel development stage. The desired tassel development stage is from the T0 to the T7 stage, for example, the T5 stage. Tassel development stages of particular interest are the optimal tassel development stage for reproductive crossing, the optimal tassel development stage for tassel sterilization or detasseling, and/or the optimal stage for administration of a development modulating treatment to a maize plant. In constructing and using a Relative Development Scale, the specific flower development stage used to construct the Relative Development Scale may be at pollen shed for about 50 percent of a population of maize plants. An exemplary range on a Relative Development Scale useful with the method of the invention is about 0.62 to about 0.75 on a Relative Development Scale.

Determinations of the timing of tassel development may be useful for agricultural methods involving planning and/or standardizing practices that are plant-development specific. Examples of this include: methods requiring the timely application of a chemical agent, such as application of an herbicide, fungicide, fertilizer, and/or growth regulator across inbreds with contrasting maturities; methods requiring monitoring, prediction, and/or adjustment of tassel development, such as monitoring male inbreds for early tassel development, which may result in decreased pollen shed, and providing appropriate treatment in order to affect tassel development; methods requiring the timely application of a hormone and/or growth regulator to correct an imbalance and/or to produce a desired agricultural result; and/or any methods requiring administering a development modulating treatment to a maize plant at said desired tassel development stage. The invention may be used in field planning and/or research work, such as for predicting work requirements associated with detasseling or plant development; for anticipating requirements linked to tassel development; for determining how stress affects tassel development; and/or for use in screening for and assessing traits and/or inbreds or hybrids by imposing stress at a specific developmental stage(s) determined by predicting the tassel development stage.

The invention provides methods useful for determining when a development modulating treatment is optimally efficacious using the Relative Development Scale. As used herein, the term "development modulating treatment" refers to the administration of at least one physical treatment and/or chemical agent that affect(s) the development of a plant. Development of a plant includes, but is not limited to, flower development, root development, leaf development, stem development, tassel development, reproductive development, gamete development, pollen development, seed development, and/or the development of any other part. The modulating treatment may cause development to be terminated, retarded, prevented, delayed, or enhanced. A development modulating treatment may be a physical treatment, such as detasseling, flaming (use of a flame torch to singe the tops of a male plant as a means of delaying maturation), and/or abrading, rubbing, scraping, scratching, cutting, piercing, sonicating, detaching, breaking, removing, crushing, pruning, and/or covering any plant part. A development modulating treatment may be a chemical agent such as natural compounds or synthetic compounds. Chemical agents that may be useful as a development modulating treatment include plant growth regulators, plant growth regulator inhibitors, plant hormones, plant hormone inhibitors, plant growth stimulators, plant growth retardants, fungicides, insecticides, herbicides, auxins, antiauxins, cytokinins, defoliants, ethylene inhibitors, ethylene releasers, gibberellins, morphactins, and gametocides. An exemplary physical treatment for use in the methods of the invention is detasseling and/or flaming. An exemplary chemical agent for use in the methods of the invention is the herbicide glyphosate. The development modulating treatment may be applied to a maize plant at any stage, for example when the tassel development stage corresponds to the range of 0.62 and 0.75 on the Relative Development Scale, which includes the tassel development stage of T5. The ability to identify the optimally efficacious period for the application of a tassel development modulating treatment using the Relative Development Scale provided is one aspect of the invention. Many tassel development modulating treatments, including chemical agents are capable of preventing development of pollen or preventing pollen shed, are known in the art and would be useful in practicing the methods of the invention.

The invention may be used for producing hybrid seed using the methods of the invention. The invention provides methods whereby a first parental maize plant is crossed with a second parental maize plant, wherein pollen production of the first parental maize plant is inhibited by application of a development modulating treatment. The methods of the invention may be used to determine a development stage and/or time for application of the development modulating treatment to be optimally efficacious. The invention may be of particular use in the methods provided in U.S. Pat. No. 6,762,344 and U.S. Patent Application Publication No. 2009/0165166. In one embodiment, the invention is a hybrid seed produced employing the methods of the invention, including plants and plant parts grown from the hybrid seed and commodity products produced therefrom.

The invention provides a method of using transgenic maize event MON 87427 plants for hybrid seed production, wherein glyphosate is used as a tassel development modulating treatment in MON 87427 plants to prevent pollen formation. This is predicated on the ability to prevent pollen shed in female parental lines comprising MON 87427 by timely application of glyphosate, thus preventing self-pollination from occurring. If the glyphosate is applied too early relative to tassel development, the male reproductive bodies may not be developed enough for the treatment to be entirely efficacious. If applied too late relative to tassel development, anther extrusion may already be underway, and the glyphosate treatment may not be able to prevent pollen development. Thus, timing of the glyphosate application relative to tassel development is important in ensuring maximum efficacy and therefore maximum purity of the hybrid seeds produced. In one embodiment, the optimal timing of glyphosate application for this method may be identified by determining the timing of tassel development of MON 87427 plants using a Relative Development Scale and selecting a range on the Relative Development Scale that indicates maturation to a desired tassel development stage. This determination of the timing of tassel development may then be used to identify the timing for administration of glyphosate as a development modulating treatment to a MON 87427 plant, thereby preventing self-fertilization and enhancing hybrid seed production. The methods of the invention reveal that tassel development in the range of 0.62 and 0.75 on the Relative Development Scale, or T5, is the optimal range for the application of glyphosate to MON 87427 plants to prevent pollen formation. Therefore, in the Roundup® Hybridization System, for any given parental female line of any given maturity group, the optimal time will be predicted by multiplying the GDUs required to achieve P50 for that parental female line by any value within that range. When the result of that calculation is equivalent to the GDU's of that growing season, the optimal glyphosate application time has been realized. Relative Development Scales may be produced using other pollen shed benchmarks, and other T-Scale benchmarks that will be similarly useful without departing from the scope of the invention.

Yet another aspect of the invention provides a method that is useful in determining the tassel development stage in which reproductive crossing is optimal. Similar to the way developmental differences across genotypes precludes reliable prediction of optimal modulating treatments based on V-Stages or GDU's alone, timing of cross-pollination may also be benefited by the Relative Development Scale. A simple study using the Relative Development Scale may reveal cross-pollination is optimal within a certain range on that scale. Again, by knowing the GDU's required for P50 of a given genotype, it will be possible to pinpoint when that range is reached without relying on unreliable vegetative benchmarks, or performing time consuming physical assessments of tassel development. Descriptions of breeding methods that are commonly used for different traits and crops can be found in one of several reference books (Allard, "Principles of Plant Breeding," John Wiley & Sons, NY, U. of CA, Davis, Calif., 50-98, 1960; Simmonds, "Principles of crop improvement," Longman, Inc., NY, 369-399, 1979; Sneep and Hendriksen, "Plant breeding perspectives," Wageningen (ed), Center for Agricultural Publishing and Documentation, 1979; Fehr, In: Soybeans: Improvement, Production and Uses, 2nd Edition, Manograph., 16:249, 1987; Fehr, "Principles of variety development," Theory and Technique, (Vol 1) and Crop Species Soybean (Vol 2), Iowa State Univ., Macmillian Pub. Co., NY, 360-376, 1987).

In practicing the methods of the invention, one or both of the maize parent plants may comprise one or more desirable trait(s) of agronomic interest. For example, a MON 87427 parent maize plant may be used in hybrid seed production for breeding with a second parent maize plant, which comprises at least one gene and/or trait of agronomic interest. In this embodiment, the Relative Development Scale may be used to monitor and/or determine the reproductive development stage of the MON 87427 parent maize plant in order to accurately time the treatment of the MON 87427 parent maize plant with glyphosate prior to pollen formation, thereby preventing self-fertilization. The event MON 87427 plants would then be pollinated by the second parent maize plant and hybrid maize seed would be harvested from the event MON 87427 plants, wherein the seed harvested from the treated MON 87427 plants has a higher yield of hybrid maize seed (i.e., higher percentage of hybrid seed harvested or higher hybrid seed purity) than maize seed harvested from untreated or an inaccurately-timed treatment of event MON 87427 plants or from other maize plant(s) under the same conditions.

Traits and genes of agronomic interest are well known in the art and include, but are not limited to, for example those for herbicide resistance, male sterility, increased yield, insect control, fungal disease resistance, virus resistance, nematode resistance, bacterial disease resistance, plant growth and development, starch production, modified and/or high oil(s) production, modified fatty acid(s) content, high protein production, fruit ripening, enhanced animal and/or human nutrition, biopolymers, environmental stress, pharmaceutical peptides and secretable peptides, improved processing traits, improved digestibility, low raffinose, industrial enzyme production, improved flavor, nitrogen fixation, hybrid seed production, fiber production, and/or biofuel production. Examples of plants having one or more desirable traits are those registered with the United States Department of Agriculture Animal and Plant Health Inspection Service (APHIS) for herbicide tolerance (e.g., maize events MON 88017, NK603, DAS-68416-4, HCEM485, DP-098140-6, P-356043-5, MIR604, 59122, TC-6275, Line 1507, MON 802, T14, and/or T25), insect control (e.g. maize events MON 863, MON 809, MON 810, MON 89034, MON 88017, MON 802, MIR-162, TC-6275, DBT418, B16, TC-1507, DAS 59122-7, MIR604, and/or MON 80100), and/or other desirable traits (e.g. maize events LY038, MON 87460, and/or 3272) (a complete listing and description of such traits is available at the United States government's website http://www.aphis.usda.gov/brs/not_reg.html).

In practicing the methods of the invention, an inbred, variety, or hybrid, or any other genotype may be used. For example, an elite inbred is a maize plant line that has resulted from breeding and selection for superior agronomic performance. The genotypes can be transformed and/or used in breeding methods to comprise a gene of agronomic interest such as glyphosate tolerance and events may be selected for suitability as a female or male parent in a hybrid seed production system.

Maize elite genotypes for use in practicing the invention, include, but are not limited to, CI9805 (U.S. Patent Publication No. 20030093826); LH321 (U.S. Patent Publication No. 20030106086); H01002 (U.S. Patent Publication No. 20030154524); HOI001 (U.S. Patent Publication No. 20030172416); 5750 (U.S. Patent Publication No. 20030177541); G0502 (U.S. Patent Publication No. 20030177543); G1102 (U.S. Patent Publication No.

20030177544); HX879 (U.S. Patent Publication No. 20040068771); 6803 (U.S. Patent Publication No. 20040088767); 5020 (U.S. Patent Publication No. 20040088768); G3001 (U.S. Patent Publication No. 20040098768); LH268 (U.S. Patent Publication No. 20040111770); LH311 (U.S. Patent Publication No. 20040111771); LH306 (U.S. Patent Publication No. 20040111772); LH351 (U.S. Patent Publication No. 20040111773); LHE323 (U.S. Patent Publication No. 20040111774); 402A (U.S. Patent Publication No. 20040123352); 366C (U.S. Patent Publication No. 20040139491); NP2315 (U.S. Patent Publication No. 20040143866); PH0GC (U.S. Patent Publication No. 20040194170); SE8505 (U.S. Patent Publication No. 20050015834); D201 (U.S. Patent Publication No. 20050028236); BE1146BMR (U.S. Patent Publication No. 20050076402); PHCAM (U.S. Patent Publication No. 20050114944); PHCK5 (U.S. Patent Publication No. 20050114945); PHC77 (U.S. Patent Publication No. 20050114951); PHCND (U.S. Patent Publication No. 20050114952); PHCMV (U.S. Patent Publication No. 20050114953); PHB00 (U.S. Patent Publication No. 20050114955); PHCER (U.S. Patent Publication No. 20050114956); PHCJP (U.S. Patent Publication No. 20050120437); PHADA (U.S. Patent Publication No. 20050120439); PHB8V (U.S. Patent Publication No. 20050120443); 6XN442 (U.S. Patent Publication No. 20050125864); 4XP811 (U.S. Patent Publication No. 20050125865); PHCCW (U.S. Patent Publication No. 20050125866); MN7224 (U.S. Patent Publication No. 20050132433); BE9514 (U.S. Patent Publication No. 20050132449); PHCA5 (U.S. Patent Publication No. 20050138697); PHCPR (U.S. Patent Publication No. 20050144687); PHAR1 (U.S. Patent Publication No. 20050144688); PHACV (U.S. Patent Publication No. 20050144689); PHEHG (U.S. Patent Publication No. 20050144690); NP2391 (U.S. Patent Publication No. 20050160487); PH8WD (U.S. Patent Publication No. 20050172367); D501 (U.S. Patent Publication No. 20050177894); D601 (U.S. Patent Publication No. 20050177896); D603 (U.S. Patent Publication No. 20050177904); PHCEG (U.S. Patent Publication No. 20050223443); W16090 (U.S. Patent Publication No. 20050273876); M10138 (U.S. Patent Publication No. 20050273877); N61060 (U.S. Patent Publication No. 20050273878); NP2460 (U.S. Patent Publication No. 20060048243); BS112 (U.S. Patent Publication No. 20060070146); PHDWA (U.S. Patent Publication No. 20060107393); PH8JV (U.S. Patent Publication No. 20060107394); PHEWW (U.S. Patent Publication No. 20060107398); PHEDR (U.S. Patent Publication No. 20060107399); PHE67 (U.S. Patent Publication No. 20060107400); PHE72 (U.S. Patent Publication No. 20060107408); PHF1J (U.S. Patent Publication No. 20060107410); PHE35 (U.S. Patent Publication No. 20060107412); PHEHR (U.S. Patent Publication No. 20060107415); PHDPP (U.S. Patent Publication No. 20060107416); PHEHC (U.S. Patent Publication No. 20060107418); PHANF (U.S. Patent Publication No. 20060107419); PHC78 (U.S. Patent Publication No. 20060107420); PH8T0 (U.S. Patent Publication No. 20060107421); PHDRW (U.S. Patent Publication No. 20060107422); PHEGV (U.S. Patent Publication No. 20060107423); PHEBA (U.S. Patent Publication No. 20060107426); PHENE (U.S. Patent Publication No. 20060112463); PHEJW (U.S. Patent Publication No. 20060112464); PHAPT (U.S. Patent Publication No. 20060112465); PHCND (U.S. Patent Publication No. 20060130188); PHCEG (U.S. Patent Publication No. 20060130189); PHADA (U.S. Patent Publication No. 20060130190); PHEED (U.S. Patent Publication No. 20060143744); PHHB (U.S. Pat. No. 5,633,427); LH262 (U.S. Pat. No. 5,633,428); LH227 (U.S. Pat. No. 5,633,429); LH226 (U.S. Pat. No. 5,639,941); LH235 (U.S. Pat. No. 5,639,942); LH234 (U.S. Pat. No. 5,639,943); PHDP0 (U.S. Pat. No. 5,639,946); PH06N (U.S. Pat. No. 5,675,066); LH177 (U.S. Pat. No. 5,684,227); PH24E (U.S. Pat. No. 5,689,034); PHP38 (U.S. Pat. No. 5,708,189); ASG06 (U.S. Pat. No. 5,714,671); CG00685 (U.S. Pat. No. 5,723,721); PHND1 (U.S. Pat. No. 5,723,722); PH44A (U.S. Pat. No. 5,723,723); ZS01591 (U.S. Pat. No. 5,723,724); ZS01101 (U.S. Pat. No. 5,723,725); ZS01452 (U.S. Pat. No. 5,723,726); ZS01429 (U.S. Pat. No. 5,723,727); ZS01819 (U.S. Pat. No. 5,723,728); ZS01250 (U.S. Pat. No. 5,723,729); ZS01595 (U.S. Pat. No. 5,723,730); CG3ND97 (U.S. Pat. No. 5,728,923); NP938(934) (U.S. Pat. No. 5,728,924); PHNG2 (U.S. Pat. No. 5,731,491); CG5NA58 (U.S. Pat. No. 5,731,502); NP948 (U.S. Pat. No. 5,731,503); LH236 (U.S. Pat. No. 5,731,504); CG00766 (U.S. Pat. No. 5,731,506); PHOAA (U.S. Pat. No. 5,750,829); PH15A (U.S. Pat. No. 5,750,830); PH25A (U.S. Pat. No. 5,750,831); PH44G (U.S. Pat. No. 5,750,832); PH0CD (U.S. Pat. No. 6,084,160); ASG25 (U.S. Pat. No. 6,084,161); 86ISI15 (U.S. Pat. No. 6,084,162); BE4547 (U.S. Pat. No. 6,084,163); PH21T (U.S. Pat. No. 6,091,007); 01DHD16 (U.S. Pat. No. 6,096,952); PH224 (U.S. Pat. No. 6,096,953); ASG26 (U.S. Pat. No. 6,103,958); ASG28 (U.S. Pat. No. 6,103,959); PH0V0 (U.S. Pat. No. 6,107,550); 90LCL6 (U.S. Pat. No. 6,111,171); 22DHD11 (U.S. Pat. No. 6,111,172); ASG17 (U.S. Pat. No. 6,114,606); AR5253bm3 (U.S. Pat. No. 6,114,609); ASG27 (U.S. Pat. No. 6,114,610); WDHQ2 (U.S. Pat. No. 6,114,611); PH3GR (U.S. Pat. No. 6,114,613); PH1NF (U.S. Pat. No. 6,118,051); PH0JG (U.S. Pat. No. 6,118,053); PH189 (U.S. Pat. No. 6,118,054); PH12J (U.S. Pat. No. 6,118,055); PH1EM (U.S. Pat. No. 6,118,056); 90DJD28 (U.S. Pat. No. 6,121,519); PH12C (U.S. Pat. No. 6,121,520); PH55C (U.S. Pat. No. 6,121,522); PH3EV (U.S. Pat. No. 6,121,523); ZS4199 (U.S. Pat. No. 6,121,525); PH2V7 (U.S. Pat. No. 6,124,529); PH4TF (U.S. Pat. No. 6,124,530); PH3 KP (U.S. Pat. No. 6,124,531); PH2MW (U.S. Pat. No. 6,124,532); PH2N0 (U.S. Pat. No. 6,124,533); PH1K2 (U.S. Pat. No. 6,124,534); PH226 (U.S. Pat. No. 6,124,535); PH2VJ (U.S. Pat. No. 6,127,609); PH1M8 (U.S. Pat. No. 6,127,610); WQCD10 (U.S. Pat. No. 6,130,369); PH1B8 (U.S. Pat. No. 6,130,370); 17DHD5 (U.S. Pat. No. 6,133,512); PH0WD (U.S. Pat. No. 6,133,513); PH3GK (U.S. Pat. No. 6,133,514); PH2VK (U.S. Pat. No. 6,137,036); PH1MD (U.S. Pat. No. 6,137,037); SM4603 (U.S. Pat. No. 6,137,038); PH04G (U.S. Pat. No. 6,140,562); NP2151 (U.S. Pat. No. 6,140,563); PH5DR (U.S. Pat. No. 6,727,413); LH254 (U.S. Pat. No. 6,730,833); PH5WB (U.S. Pat. No. 6,730,834); PH7CH (U.S. Pat. No. 6,730,835); PH54M (U.S. Pat. No. 6,730,836); PH726 (U.S. Pat. No. 6,730,837); PH48V (U.S. Pat. No. 6,734,348); PH3PV (U.S. Pat. No. 6,737,566); PH77V (U.S. Pat. No. 6,740,795); PH7JB (U.S. Pat. No. 6,740,796); NP2316 (U.S. Pat. No. 6,740,797); PH70R (U.S. Pat. No. 6,740,798); RAA1 (U.S. Pat. No. 6,747,194); VMM1 (U.S. Pat. No. 6,747,195); PH3RC (U.S. Pat. No. 6,747,196); MNI1 (U.S. Pat. No. 6,753,465); 5750 (U.S. Pat. No. 6,756,527); PH6 KW (U.S. Pat. No. 6,756,528); PH951 (U.S. Pat. No. 6,756,530); PH6ME (U.S. Pat. No. 6,759,578); NP2171 (U.S. Pat. No. 6,759,579); PH87H (U.S. Pat. No. 6,759,580); PH26N (U.S. Pat. No. 6,765,132); RII1 (U.S. Pat. No. 6,765,133); PH9AH (U.S. Pat. No. 6,770,802); PH51H (U.S. Pat. No.

6,774,289); PH94T (U.S. Pat. No. 6,774,290); PH7AB (U.S. Pat. No. 6,777,599); PH5FW (U.S. Pat. No. 6,781,042); PH75K (U.S. Pat. No. 6,781,043); KW7606 (U.S. Pat. No. 6,784,348); PH8CW (U.S. Pat. No. 6,784,349); PH8PG (U.S. Pat. No. 6,784,350); RBO1 (U.S. Pat. No. 6,797,869); 9SM990 (U.S. Pat. No. 6,803,509); PH5TG (U.S. Pat. No. 6,806,408); I501150 (U.S. Pat. No. 6,806,409); I390186 (U.S. Pat. No. 6,806,410); PH6JM (U.S. Pat. No. 6,809,240); KW4636 (U.S. Pat. No. 6,809,243); I363128 (U.S. Pat. No. 6,809,244); LH246 (U.S. Pat. No. 6,812,386); 2JK221 (U.S. Pat. No. 6,812,387); PHN46 (U.S. Pat. No. 5,567,861); ZS0223 (U.S. Pat. No. 5,569,813); phajo (U.S. Pat. No. 5,569,816); PHJJ3 (U.S. Pat. No. 5,569,817); phap8 (U.S. Pat. No. 5,569,818); PHPP8 (U.S. Pat. No. 5,569,819); ZS1284 (U.S. Pat. No. 5,569,820); PHT11 (U.S. Pat. No. 5,569,821); phte4 (U.S. Pat. No. 5,569,822); ZS0114 (U.S. Pat. No. 5,569,826); 7054 (U.S. Pat. No. 5,576,473); ZS0560 (U.S. Pat. No. 5,585,533); ZS0853 (U.S. Pat. No. 5,585,534); ZS1791 (U.S. Pat. No. 5,585,539); ZS1513 (U.S. Pat. No. 5,585,541); ZS1679 (U.S. Pat. No. 5,589,606); ZS1022 (U.S. Pat. No. 5,602,314); ZS1202 (U.S. Pat. No. 5,602,315); ZS1783 (U.S. Pat. No. 5,602,316); PHDG1 (U.S. Pat. No. 5,602,318); PHKV1 (U.S. Pat. No. 5,608,138); PHO5F (U.S. Pat. No. 5,608,139); PH38B (U.S. Pat. No. 5,608,140); PH42B (U.S. Pat. No. 5,618,987); PHDD6 (U.S. Pat. No. 5,625,129); ZS0541 (U.S. Pat. No. 5,625,131); PH08B (U.S. Pat. No. 5,625,132); PHOC7 (U.S. Pat. No. 5,625,133); LH233 (U.S. Pat. No. 5,625,135); ASG05 (U.S. Pat. No. 5,723,731); LH281 (U.S. Pat. No. 5,723,739); PHBF0 (U.S. Pat. No. 5,728,919); CG5NA01 (U.S. Pat. No. 5,728,922); AR5651bm3 (U.S. Pat. No. 5,977,458); LH266 (U.S. Pat. No. 5,977,459); LH303 (U.S. Pat. No. 5,977,460); LH301 (U.S. Pat. No. 5,981,855); 4SQ601 (U.S. Pat. No. 5,986,182); PH1TB (U.S. Pat. No. 5,986,184); PH24D (U.S. Pat. No. 5,986,185); LH229 (U.S. Pat. No. 5,986,186); LH277 (U.S. Pat. No. 5,986,187); PH1CN (U.S. Pat. No. 5,990,393); LH261 (U.S. Pat. No. 5,990,394); W1498A (U.S. Pat. No. 5,990,395); WQDS2 (U.S. Pat. No. 5,994,631); NL085B (U.S. Pat. No. 5,998,710); PH09E (U.S. Pat. No. 5,998,711); LH284 (U.S. Pat. No. 6,015,944); PH1B5 (U.S. Pat. No. 6,020,543); PH1CA (U.S. Pat. No. 6,025,547); 7OLDL5 (U.S. Pat. No. 6,031,160); GM9215 (U.S. Pat. No. 6,031,161); 90LDI1 (U.S. Pat. No. 6,031,162); 90LDC2 (U.S. Pat. No. 6,034,304); 90QDD1 (U.S. Pat. No. 6,034,305); R398D (U.S. Pat. No. 6,034,306); RDBQ2 (U.S. Pat. No. 6,037,531); HX621 (U.S. Pat. No. 6,040,506); HX622 (U.S. Pat. No. 6,040,507); 01HG12 (U.S. Pat. No. 6,040,508); HX740 (U.S. Pat. No. 6,043,416); 79314N1 (U.S. Pat. No. 6,043,417); 17INI20 (U.S. Pat. No. 6,043,418); 17DHD7 (U.S. Pat. No. 6,046,387); 83INI8 (U.S. Pat. No. 6,046,388); 83InI14 (U.S. Pat. No. 6,046,389); 01INL1 (U.S. Pat. No. 6,046,390); LH286 (U.S. Pat. No. 6,049,030); ASG29 (U.S. Pat. No. 6,054,640); ASG07 (U.S. Pat. No. 6,060,649); QH111 (U.S. Pat. No. 6,069,303); 09DSQ1 (U.S. Pat. No. 6,072,108); JCRNR113 (U.S. Pat. No. 6,072,109); NP2029 (U.S. Pat. No. 6,072,110); ASG09 (U.S. Pat. No. 6,077,996); PHOWE (U.S. Pat. No. 6,077,997); 86AQV2 (U.S. Pat. No. 6,077,999); PH1GG (U.S. Pat. No. 6,080,919); RPK7346 (U.S. Pat. No. 6,506,965); NP2044BT (U.S. Pat. No. 6,573,438); PH8W4 (U.S. Pat. No. 6,600,095); M42618 (U.S. Pat. No. 6,617,500); MV7100 (U.S. Pat. No. 6,624,345); 3JP286 (U.S. Pat. No. 6,627,800); BE4207 (U.S. Pat. No. 6,632,986); CI9805 (U.S. Pat. No. 6,632,987); JCR503 (U.S. Pat. No. 6,635,808); NR401 (U.S. Pat. No. 6,635,809); 4VP500 (U.S. Pat. No. 6,635,810); 7SH385 (U.S. Pat. No. 6,642,440); KW4773 (U.S. Pat. No. 6,642,441); NP2073 (U.S. Pat. No. 6,646,187); PSA104 (U.S. Pat. No. 6,646,188); 5XH755 (U.S. Pat. No. 6,653,536); 1445-008-1 (U.S. Pat. No. 6,653,537); NP2015 (U.S. Pat. No. 6,657,109); 7SH383 (U.S. Pat. No. 6,660,916); LH310 (U.S. Pat. No. 6,664,451); I880S (U.S. Pat. No. 6,670,531); RR728-18 (U.S. Pat. No. 6,677,509); LH320 (U.S. Pat. No. 6,683,234); 11084BM (U.S. Pat. No. 6,686,519); W60028 (U.S. Pat. No. 6,686,520); PH1GD (U.S. Pat. No. 6,693,231); LH295 (U.S. Pat. No. 6,693,232); PH1BC (U.S. Pat. No. 6,700,041); PH4V6 (U.S. Pat. No. 6,706,954); NP2276 (U.S. Pat. No. 6,706,955); NP2222 (U.S. Pat. No. 6,710,233); PhR08 (U.S. Pat. No. 6,717,036); PH581 (U.S. Pat. No. 6,717,037); PH6WR (U.S. Pat. No. 6,717,038); PH5HK (U.S. Pat. No. 6,717,039); PH5W4 (U.S. Pat. No. 6,717,040); PH0KT (U.S. Pat. No. 6,720,486); PH4GP (U.S. Pat. No. 6,720,487); PHJ8R (U.S. Pat. No. 6,723,900); NP2052 (U.S. Pat. No. 6,723,901); PH7CP (U.S. Pat. No. 6,723,902); PH6WG (U.S. Pat. No. 6,723,903); PH54H (U.S. Pat. No. 6,727,412); 4P33339 (U.S. Pat. No. 5,489,744); PHKM5 (U.S. Pat. No. 5,491,286); LH225 (U.S. Pat. No. 5,491,293); LH185 (U.S. Pat. No. 5,491,294); LH176 (U.S. Pat. No. 5,491,296); PHW06 (U.S. Pat. No. 5,495,065); LH252 (U.S. Pat. No. 5,495,067); LH231 (U.S. Pat. No. 5,495,068); PHTE4 (U.S. Pat. No. 5,495,069); PHP38 (U.S. Pat. No. 5,506,367); PHN82 (U.S. Pat. No. 5,506,368); PHTD5 (U.S. Pat. No. 5,527,986); 899 (U.S. Pat. No. 5,530,181); PHAP1 (U.S. Pat. No. 5,530,184); PHKW3 (U.S. Pat. No. 5,534,661); CG00653 (U.S. Pat. No. 5,536,900); PHRD6 (U.S. Pat. No. 5,541,352); PHK46 (U.S. Pat. No. 5,543,575); PHBG4 (U.S. Pat. No. 5,545,809); LH189 (U.S. Pat. No. 5,545,811); PHNJ2 (U.S. Pat. No. 5,545,812); PHRF5 (U.S. Pat. No. 5,545,813); PHFR8 (U.S. Pat. No. 5,545,814); PHN18 (U.S. Pat. No. 5,557,034); PHTP9 (U.S. Pat. No. 5,557,038); PH54B (U.S. Pat. No. 5,563,320); PHGF5 (U.S. Pat. No. 5,563,321); PHAG6 (U.S. Pat. No. 5,563,322); PHAP9 (U.S. Pat. No. 5,563,323); PHBE2 (U.S. Pat. No. 5,563,325); ZS0510 (U.S. Pat. No. 5,563,327); PHAAO (U.S. Pat. No. 5,602,317); LH273 (U.S. Pat. No. 5,880,348); 7571 (U.S. Pat. No. 5,880,349); LH237 (U.S. Pat. No. 5,880,350); PH0B4 (U.S. Pat. No. 5,889,188); FEBS (U.S. Pat. No. 5,902,922); 8F286 (U.S. Pat. No. 5,905,191); 3AZA1 (U.S. Pat. No. 5,910,625); 91DFA-5 (U.S. Pat. No. 5,910,635); ASG20 (U.S. Pat. No. 5,910,636); ZS03940 (U.S. Pat. No. 5,912,420); 91ISI6 (U.S. Pat. No. 5,912,421); MF1113B (U.S. Pat. No. 5,914,452); PH03D (U.S. Pat. No. 5,917,125); PHDN7 (U.S. Pat. No. 5,917,134); 01DIB2 (U.S. Pat. No. 5,920,003); 82DHB1 (U.S. Pat. No. 5,922,935); 8M222 (U.S. Pat. No. 5,922,936); PHMJ2 (U.S. Pat. No. 5,929,313); SBB1 (U.S. Pat. No. 5,932,787); 86ISI3 (U.S. Pat. No. 5,932,788); ZS01231 (U.S. Pat. No. 5,936,144); 87DIA4 (U.S. Pat. No. 5,936,145); 79310J2 (U.S. Pat. No. 5,936,146); PH1GC (U.S. Pat. No. 5,936,148); 01DHD10 (U.S. Pat. No. 5,939,606); PH2CB (U.S. Pat. No. 5,939,607); PH080 (U.S. Pat. No. 5,939,608); PH14T (U.S. Pat. No. 5,942,670); PH185 (U.S. Pat. No. 5,942,671); PH19V (U.S. Pat. No. 5,948,957); ZS09247 (U.S. Pat. No. 5,952,551); CRAUGSH2W-89 (U.S. Pat. No. 5,952,552); 91DHA1 (U.S. Pat. No. 5,962,770); LH300 (U.S. Pat. No. 5,965,798); 91ISI4 (U.S. Pat. No. 5,965,799); 79103A1 (U.S. Pat. No. 5,969,212); ASG22 (U.S. Pat. No. 5,969,220); 82IUH1 (U.S. Pat. No. 5,969,221); (U.S. Pat. No. 5,969,222); LH302 (U.S. Pat. No. 5,973,238); LH265 (U.S. Pat. No. 5,973,239); PHFW4 (U.S. Pat. No. 5,977,451); 01IBH10 (U.S. Pat. No. 5,977,452); 91CSI-1 (U.S. Pat. No. 5,977,453); WKBC5 (U.S. Pat. No. 5,977,455); PH1M7 (U.S. Pat. No. 5,977,456); R327H (U.S. Pat. No. 6,399,860); FR2108 (U.S. Pat. No. 6,407,320); FR3383 (U.S. Pat. No. 6,410,830); IT302 (U.S. Pat. No. 6,414,227); FR3303 (U.S. Pat. No. 6,414,228); 9034 (U.S. Pat. No. 6,420,634); G1500 (U.S. Pat. No. 6,420,635); FR3311 (U.S. Pat.

No. 6,420,636); I389972 (U.S. Pat. No. 6,420,637); PH77C (U.S. Pat. No. 6,423,888); IT201 (U.S. Pat. No. 6,426,451); G3000 (U.S. Pat. No. 6,426,453); 94INK1B (U.S. Pat. No. 6,429,363); PH3HH (U.S. Pat. No. 6,433,259); 6TR512 (U.S. Pat. No. 6,433,260); 89AHD12 (U.S. Pat. No. 6,433,261); I889291 (U.S. Pat. No. 6,433,262); 2070BT (U.S. Pat. No. 6,437,223); 3323 (U.S. Pat. No. 6,437,224); G1900 (U.S. Pat. No. 6,441,279); 161UL6 (U.S. Pat. No. 6,441,280); 7RN401 (U.S. Pat. No. 6,444,881); UBB3 (U.S. Pat. No. 6,444,882); 6077 (U.S. Pat. No. 6,444,883); I014738 (U.S. Pat. No. 6,444,884); TDC1 (U.S. Pat. No. 6,452,074); GF6151 (U.S. Pat. No. 6,452,075); 7180 (U.S. Pat. No. 6,452,076); WQDS7 (U.S. Pat. No. 6,455,764); X532Y (U.S. Pat. No. 6,459,021); I465837 (U.S. Pat. No. 6,459,022); 1784S (U.S. Pat. No. 6,469,232); LH176Bt810 (U.S. Pat. No. 6,469,233); 6RC172 (U.S. Pat. No. 6,469,234); 3327 (U.S. Pat. No. 6,469,235); 7SH382 (U.S. Pat. No. 6,476,298); I181664 (U.S. Pat. No. 6,476,299); NP2010 (U.S. Pat. No. 6,483,014); FR3361 (U.S. 3Pat. No. 6,483,015); 1778S (U.S. Pat. No. 6,486,386); I362697 (U.S. Pat. No. 6,492,581); RPK7250 (U.S. Pat. No. 6,506,964); and 6RT321 (U.S. Pat. No. 6,911,588).

As used herein, the term "comprising" means "including but not limited to".

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1

Transformation of Maize and MON 87427 Event Selection

The maize plant MON 87427 was produced by *Agrobacterium*-mediated transformation of maize. Maize cells were transformed and regenerated into intact maize plants and individual plants were selected from the population of plants that showed integrity of the transgene expression cassette and resistance to glyphosate. From this population, maize plant event MON 87427 was selected and characterized.

The transgenic glyphosate tolerant maize plant MON 87427 was developed through *Agrobacterium*-mediated transformation of maize immature embryos utilizing transformation vector pMON58401. The transgene insert and expression cassette of MON 87427 comprises the promoter and leader from the cauliflower mosaic virus (CaMV) 35S containing a duplicated enhancer region (P-e35S); operably linked to a DNA leader derived from the first intron from the maize heat shock protein 70 gene (I-HSP70); operably linked to a DNA molecule encoding an N-terminal chloroplast transit peptide from the shkG gene from *Arabidopsis thaliana* EPSPS (Ts-CTP2); operably linked to a DNA molecule derived from the aroA gene from the *Agrobacterium* sp. strain CP4 and encoding the CP4 EPSPS protein; operably linked to a 3' UTR DNA molecule derived from the nopaline synthase (T-NOS) gene from *Agrobacterium tumefaciens*.

Maize cells can be transformed by a variety of methods. For example, the following method can be used to produce a transgenic maize plant comprising the plant expression cassette of the invention. Liquid cultures of *Agrobacterium tumefaciens* containing the plant expression cassette are initiated from glycerol stocks or from a freshly streaked plate and grown overnight at 26° C.-28° C. with shaking (approximately 150 revolutions per minute, rpm) to mid-log growth phase in liquid LB medium, pH 7.0, containing 50 mg/l (milligram per liter) kanamycin, and either 50 mg/l streptomycin or 50 mg/l spectinomycin, and 25 mg/l chloramphenicol with 200 μM acetosyringone (AS). The *Agrobacterium* cells are resuspended in the inoculation medium (liquid CM4C, as described in Table 8 of U.S. Pat. No. 6,573,361) and the cell density is adjusted such that the resuspended cells have an optical density of 1 when measured in a spectrophotometer at a wavelength of 660 nm (i.e., $OD_{660}$). Freshly isolated immature maize embryos are inoculated with *Agrobacterium* and co-cultured 2-3 days in the dark at 23° C. The embryos are then transferred to delay media (N6 1-100-12; as described in Table 1 of U.S. Pat. No. 5,424,412) supplemented with 500 mg/l Carbenicillin (Sigma-Aldrich, St Louis, Mo.) and 20 μM $AgNO_3$) and incubated at 28° C. for 4 to 5 days. All subsequent cultures are kept at this temperature.

The embryos are transferred to the first selection medium (N61-0-12, as described in Table 1 of U.S. Pat. No. 5,424,412), supplemented with 500 mg/l Carbenicillin and 0.5 mM glyphosate. Two weeks later, surviving tissues are transferred to the second selection medium (N61-0-12) supplemented with 500 mg/l Carbenicillin and 1.0 mM glyphosate. Surviving callus is subcultured every 2 weeks for about 3 subcultures on 1.0 mM glyphosate. When glyphosate tolerant tissues are identified, the tissue is bulked up for regeneration. For regeneration, callus tissues are transferred to the regeneration medium (MSOD, as described in Table 1 of U.S. Pat. No. 5,424,412) supplemented with 0.1 μM abscisic acid (ABA; Sigma-Aldrich, St Louis, Mo.) and incubated for two weeks. The regenerating calli are transferred to a high sucrose medium and incubated for two weeks. The plantlets are transferred to MSOD media (without ABA) in a culture vessel and incubated for two weeks. Rooted plants with normal phenotypic characteristics are selected and transferred to soil for growth and further assessment. The R0 plants generated through the above transformation are transferred to soil for growth and then selfed to produce R1 seed. Plants are selected by a combination of analytical techniques, including TaqMan, PCR analysis, and herbicide spray.

The MON 87427 event was selected from 45 individual transgenic events based on multi-year analyses demonstrating the superior phenotypic and molecular characteristics of the event and its desirable haplotype association (Cr 9, 60 cM). The selection process for event MON 87427 began with transformed maize plants representing 45 R0 events. These were sprayed with glyphosate (64 oz/acre at V7) and then evaluated for vegetative tolerance and post-glyphosate spray sterility. Of the initial 45 events, 35 R0 events exhibited vegetative glyphosate tolerance and were male sterile when sprayed with the tested rate and timing of glyphosate. Plants of these 35 R0 events were then advanced for further characterization by molecular analysis. Using Taqman® PCR analysis and Southern blot analysis, the 35 events were molecularly characterized. Of the 35 events analyzed, 29 events were selected for further advancement and field testing. The 29 R1 events were then analyzed in field trials for field efficacy and yield. In addition to this, additional molecular characterization, including genomic and protein expression characterization, was done. Data were analyzed and from the comprehensive R1 plant analysis and the field trial results, three lead events were selected and advanced to R2 field testing. Subsequent analysis and testing of these 3 lead events led to the selection of event MON 87427.

Additional field screening included treating event MON 87427 with glyphosate at 32 oz/acre (Roundup Ultra®, Monsanto Co., St. Louis, Mo.) at vegetative 4 growth stage (V4) and vegetative 10 growth stage (V10). Positive and negative plant counts were taken after the V4 spray. Additionally, treated plants were scored for chlorosis and malformation at 10-14 days after treatment (DAT) following both the V4 and V10 spray. Tassel sterility ratings at flowering were also scored for the plants sprayed at V4 and V10.

Example 2

Characterization of MON 87427 DNA Sequences

The DNA inserted into the genome of maize plant MON 87427 and the flanking genomic sequence was characterized by detailed molecular analyses. These analyses included: sequencing the transgene insert DNA and the genomic DNA flanking the transgene insert, determining the transgene insert number (number of integration sites within the maize genome), determining the copy number (number of copies of transgene DNA within one locus), analyzing the integrity of the inserted gene cassette, analyzing the genomic DNA flanking the insert and the association of the insertion with haplotype regions of the maize genome.

Sequences flanking the transgene DNA insertion in MON 87427 were determined using PCR techniques. Plant genomic DNA was isolated from the transgenic line from tissue grown under standard greenhouse conditions. Plant tissue was combined with liquid nitrogen and ground to a fine powder using a mortar and pestle. DNA was extracted using a Nucleon™ PhytoPure™ Genomic DNA extraction kit (RPN8511, Amersham, Piscataway, N.J.) according to the manufacturer's protocol. After the final precipitation step, DNA was resuspended in 0.5 ml of TE (10 mM Tris-HCl pH 8.0, 1 mM EDTA). This method can be modified by one skilled in the art to extract DNA from any tissue of maize, including, but not limited to, seed. An aliquot of DNA was digested with restriction endonucleases selected based upon restriction analysis of the transgene DNA. After self-ligation of restriction fragments, PCR was performed using primers designed from the transgene DNA sequence that would amplify sequences extending away from the 5' and 3' ends of the transgene DNA. PCR products were separated by agarose gel electrophoresis and purified using a QIAGEN gel purification kit (Qiagen, Valencia, Calif.). The subsequent DNA products were sequenced directly using standard DNA sequencing protocols. The 5' flanking sequence which extends into the right border (RB) sequence of the expression cassette transgene DNA is presented as SEQ ID NO: 7. The 3' flanking sequence which extends into the left border (LB) sequence of the expression cassette transgene DNA is presented as SEQ ID NO: 8. The sequence fully integrated into the maize genomic DNA and containing the expression cassette DNA is presented as SEQ ID NO: 9.

Isolated DNA molecule sequences were compared to the transgene DNA sequence to identify the flanking sequence and the co-isolated transgene DNA fragment. Confirmation of the presence of the expression cassette was achieved by PCR with primers designed based upon the deduced flanking sequence data and the known transgene DNA sequence. The wild type sequence corresponding to the same region in which the transgene DNA was integrated in the transformed line was isolated using primers designed from the flanking sequences in MON 87427. The PCR reactions were performed using the Elongase® amplification system (Invitrogen, Carlsbad, Calif.). The flanking DNA sequences in MON 87427 and the wild type sequence LH198 were analyzed against multiple nucleotide and protein databases. This information was used to examine the relationship of the transgene to the plant genome and to look for the insertion site integrity.

Example 3

Methods Useful for Identification of MON87427 DNA in a Sample

This example describes methods useful to identify event MON 87427 DNA in a sample. The event flanking sequence(s), wild-type maize genomic sequence, and/or the transgene sequence may be used to design primers and probes for use in such methods. Internal control primer(s) and probe(s) may or may not be included in an assay.

Endpoint TAQMAN® thermal amplification methods to identify event MON 87427 (event-specific assay) and/or the CP4-EPSPS synthetic gene (a.k.a. CP4-Zm) (transgene-specific assay) of event MON 87427 in a sample are described. The event flanking sequence(s), wild-type maize genomic sequence, and the transgene sequence were used to design primers and probes for use in these assays (Table 1). The DNA primers used in the event-specific assay are primers SQ12763 (SEQ ID NO: 17) and SQ12886 (SEQ ID NO: 18) with 6-FAM™ labeled probe PB4352 (SEQ ID NO: 19). The DNA primers used in the transgene-specific assay are primers SQ20052 (SEQ ID NO: 11) and SQ20053 (SEQ ID NO: 12) with 6-FAM™ labeled probe PB10016 (SEQ ID NO: 13). 6-FAM™ is a fluorescent dye product of Applied Biosystems (Foster City, Calif.) attached to the DNA probe. The controls for this analysis should include a positive control from maize containing event MON 87427 DNA, a negative control from non-transgenic maize, and a negative control that contains no template DNA.

Additionally, an optional control for the PCR reaction may include Internal Control Primers and an Internal Control Probe, specific to a single copy gene in the maize genome. One of skill in the art will know how to design primers specific to a single copy gene in the maize genome. The DNA primers used in the transgene-specific assay as internal controls are primers SQ1241 (SEQ ID NO: 14) and SQ1242 (SEQ ID NO: 15) with VIC TAMRA labeled probe PB0084 (SEQ ID NO: 16). For the transgene-specific assay internal control primers and probe may be used with optional steps 5-6 below. For the event-specific assay no internal control is used.

TABLE 1

Primers and Probes

| Description | Name | SEQ ID NO | Sequence |
|---|---|---|---|
| CP4Zm Primer-Probes | | | |
| Transgene Primer-1 | SQ20052 | 11 | GGCAACCGCTCGCAAAT |
| Transgene Primer-2 | SQ20053 | 12 | ATCGCCCGGAATCCTGA |
| Transgene 6-FAM ™ Probe | PB10016 | 13 | 6FAM-TTCCGGCCTTTCGGGAA |

TABLE 1-continued

Primers and Probes

| Description | Name | SEQ ID NO | Sequence |
|---|---|---|---|
| Internal Control | SQ1241 | 14 | GCCTGCCGCAGACCAA |
| Internal Control | SQ1242 | 15 | CAATGCAGAGCTCAGCTTCATC |
| Internal Control VIC Probe | PB0084 | 16 | VIC-TCCAGTACGTGCAGTCCCTCC TCCCT-TAMRA |
| MON 87427 Primer-Probes | | | |
| Event Primer-1 | SQ12763 | 17 | CGGAAACGGTCGGGTCA |
| Event Primer-2 | SQ12886 | 18 | CTCCATATTGACCATCATACTCATTGC |
| Event 6-FAM ™ Probe | PB4352 | 19 | 6FAM-AATGTAGAAAATCGGGACAAT-MGBNFQ |

Examples of conditions useful with Endpoint TAQMAN® methods are as follows:

Step 1: 18 megohm water adjusted for final volume of 10 µl.

Step 2: 5.0 µl of 2× Universal Master Mix (dNTPs, enzyme, buffer) to a 1× final concentration.

Step 3: 0.5 µl Event Primer-1 (SEQ ID NO: 17) and Event Primer-2 (SEQ ID NO: 18) Mix (resuspended in 18 megohm water to a concentration of 20 uM for each primer) to 1.0 µM final concentration (for example in a microcentrifuge tube, the following should be added to achieve 500 µl at a final concentration of 20 uM: 100 µl of Event Primer-1 (SEQ ID NO: 17) at a concentration of 100 µM; 100 µl of Event Primer-2 (SEQ ID NO: 18) at a concentration of 100 µM; 300 µl of 18 megohm water).

Step 4: 0.2 µl Event 6-FAM™ MGB Probe (SEQ ID NO: 19) (resuspended in 18 megohm water to a concentration of 10 µM) to 0.2 µM final concentration.

Step 5 (Optional): 0.5 µl Internal Control Primer-1 and Internal Control Primer-2 Mix (resuspended in 18 megohm water to a concentration of 20 µM for each primer) to 1.0 µM final concentration.

Step 6 (Optional): 0.2 µl Internal Control VIC™ Probe to 0.2 µM final concentration (resuspended in 18 megohm water to a concentration of 10 µM)

Step 7: 3.0 µl Extracted DNA (template) for each sample with one each of the following comprising 1. Leaf Samples to be analyzed; 2. Negative control (non-transgenic DNA); 3. Negative water control (no template); 4. Positive control MON 87427 DNA.

Step 8: Thermocycler Conditions as follows: One Cycle at 50° C. for 2 minutes; One Cycle at 95° C. for 10 minutes; Ten Cycles of (95° C. for 15 seconds then 64° C. for 1 minute with −1° C./cycle); Thirty Cycles of (95° C. for 15 seconds then 54° C. 1 minute); final cycle of 10° C.

These assays are optimized for use with either an Applied Biosystems GeneAmp® PCR System 9700 (run at maximum speed) or MJ Research DNA Engine PTC-225 thermal cycler. Other methods and apparatus known to those skilled in the art that produce amplicons that identify the event MON 87427 DNA is within the skill of the art.

SEQ ID NO: 11 and SEQ ID NO: 12 or SEQ ID NO: 17 and SEQ ID NO: 18, are each an example of a pair of DNA molecules (a primer pair) consisting of a first DNA molecule and a second DNA molecule different from the first DNA molecule, wherein said first and second DNA molecules each comprise a nucleic acid molecule having a nucleotide sequence of sufficient length of contiguous nucleotides of SEQ ID NO: 10 to function as DNA primers when used together in an amplification reaction with DNA derived from event MON 87427 to produce an amplicon diagnostic for MON 87427 DNA in a sample. These primers may be used in other polymerase chain reaction (PCR) based methods for detecting the event.

Example 4

Use of Event MON 87427 for Hybrid Seed Production

The following example describes how one may use the MON 87427 for maize breeding purposes including using the methods described in U.S. Patent Publication No. 20090165166 and/or in U.S. Pat. No. 7,314,970.

In hybrid seed production, maize plants comprising MON 87427 are planted in an area, such as an open field. Other parent maize plant(s) may or may not be present in the same area. For weed control during seed production and in commercial fields, glyphosate may be applied to maize plants comprising MON 87427 at vegetative stages as directed on Roundup® agricultural product labels, at the same rates used in Roundup Ready® maize events NK603 and MON 88017. For hybrid seed production, two glyphosate applications beginning just prior and/or during tassel development stages (approximate maize vegetative growth stages ranging from V8 to V13) are applied to the MON 87427 plants to produce a male sterile phenotype through tissue-selective glyphosate tolerance. In a hybrid maize seed production system, the MON 87427 plants with glyphosate applied at tassel development timings will be male sterile and thus can be readily pollinated by other pollen donor (male) plants, resulting in viable hybrid maize seed carrying the gene for tissue-selective glyphosate tolerance. The pollen donor plants may or may not be present in the same area. Pollination may be affected by any means known in the art, including by proximity placement of plants or by hand pollination. Only specifically timed glyphosate applications beginning just prior to and/or during tassel development stages (approximate maize vegetative growth stages ranging from V8 to V13) will produce a male sterile phenotype through tissue-selective glyphosate tolerance in MON 87427. Glyphosate is a systemic herbicide that is readily translocated via the phloem in plants. Once glyphosate is in the phloem, it moves to areas of high meristematic activity, following a typical source to sink distribution. Pollen development in a maize plant takes approximately four weeks to complete. Early tassel growth stages start at the approximate maize vegetative growth stage V9, therefore glyphosate applications made at approximately this stage and time allow maximum translocation of glyphosate to the male reproductive tissues. Glyphosate applications made during early vegetative stages, consistent with the application timing specified in the current Roundup® agricultural product label for weed control purposes, do not affect pollen production of MON 87427 because the sensitive male reproductive tissues are not actively developing at that time. Modifications can be made to the glyphosate treatment conditions that are known by those in the art of herbicide application and are within the scope of invention.

Figure 2:
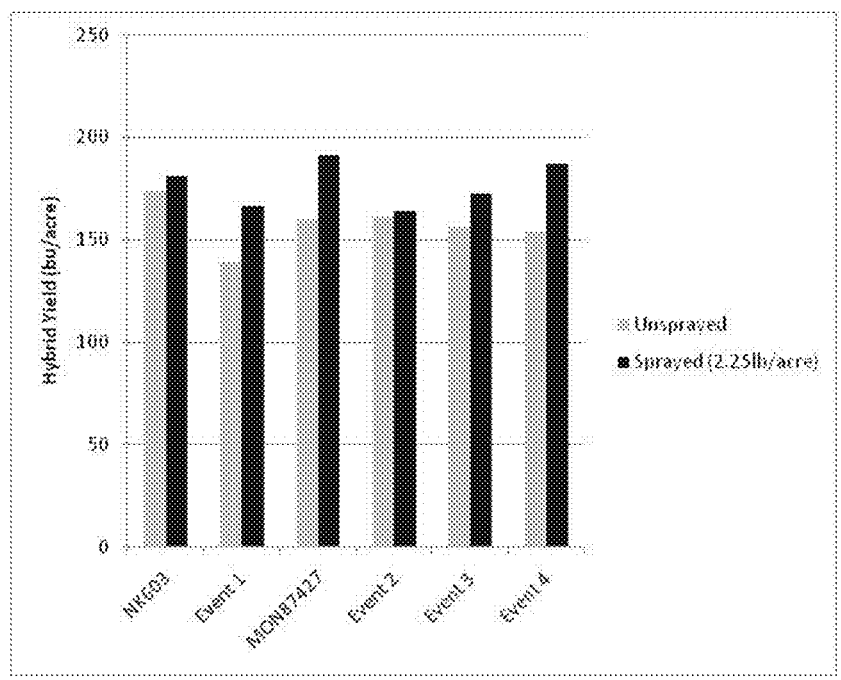
FIG. 2 shows the seed yield of hybrids of MON 87427 when crossed with maize event NK603 and sprayed twice per season with glyphosate at a rate of 2.25 pounds per acre each spray.

MON 87427 when crossed with another glyphosate tolerant maize event such as maize event NK603 (U.S. Pat. No. 6,825,400) to produce hybrid seed shows no yield loss when compared to yield from the conventional NK603 hybrid (see FIG. 2). A field of hybrid maize plants were treated with glyphosate in two successive sprays at 2.25 lb a.e./acre each for weed control and no difference was observed in injury or male fertility between the various event MON 87427 hybrids and the NK603 hybrid. This illustrates that the F1 hybrid plants from event MON 87427 crosses are fully tolerant to glyphosate when used for weed control.

Example 5

Measuring Tassel Development Stages

Tassel development stages are illustrated in FIG. 3, with approximate size in millimeters shown between brackets. In the figure, Vg is meristem at vegetative stage; T0 is switch from vegetative to reproductive; T1 is reproductive growing point visible (0.9 mm); T2 is lateral branch primordia visible (1.8 mm); T3 is spikelet primordia visible (4.1 mm); T4 is central axis and lateral axis elongation (12.9 mm); T5 is beginning of anthers differentiation (41.0 mm); T6 is beginning of pollen differentiation (175 mm); and T7 is anther exertion and pollen shed (285.0 mm). The tassel development stage of a given plant was measured by examining the tassel at various stages of maturation. Using a scalpel and fine forceps under a dissecting scope, the tassel meristem was dissected away from the developing leaves. The meristem was then cut at its base with the scalpel and assessed according to the tassel development stages (shown in FIG. 3) by looking through a microscope.

Example 6

Vegetative Development Stage (V-Stage) Relative to Tassel Development Stage

This example demonstrates that tassel dry weight, tassel length, and tassel development stage vary significantly across genotypes when measured relative to plant vegetative stages and plant vegetative growth.

Ten genotypes were planted: inbred lines LH198, LH287, O1DKD2, 19HGZI, 17IDI6 and hybrids DKC 44-46, DKC 47-10, DKC 52-40, DKC 58-80, DKC 63-81. The hybrids were selected to be representative of genetics that would present a different pattern of development. The study was conducted in Farmer City (IL), Kearney (NE), and Williamsburg (IA). The ten genotypes were planted with a cone planter and thinned to a final stand of 38,000 plants per acre. Plot length was 20 feet with 3 feet alleys by four rows to ensure enough plants for all treatments and reduce border effects. Data were collected to record both plant vegetative development and tassel development observations relative to the tassel development stages.

Figure 4:
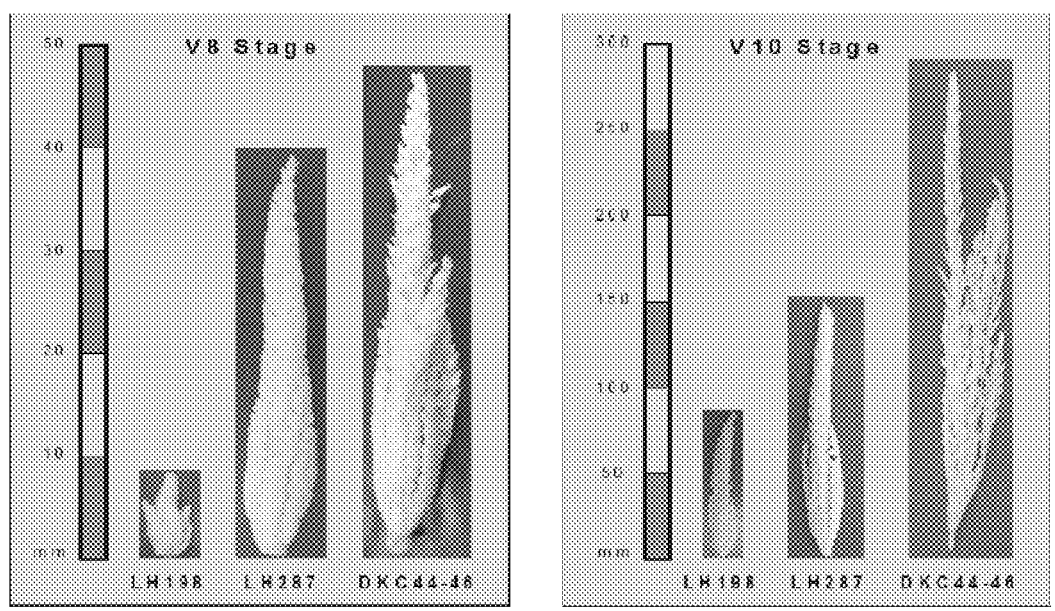
FIG. 4 illustrates tassel size variation between three maize genotypes at two developmental stages (V8 and V10).

Distinct differences in tassel development were observed among genotypes at identical respective vegetative stages (V-Stages). For example, tassel size differences between genotypes were evident at every V-stage. The average tassel length at V8 stage was 7 mm for LH198, 40.2 mm for LH287, and 47.8 mm for DKC44-46 (FIG. 4). This range in tassel length size at the V8 stage represents up to a 7-fold difference between the genotypes. At the V10 stage, the average tassel lengths for these three genotypes were 70.1 mm, 148.2 mm, and 277.3 mm, respectively (FIG. 4). This resulted in a range of almost 4 fold difference between the genotypes. Genetic variation in tassel growth relative to V-stages is also obvious when examining tassel dry weight accumulation.

In a further study, seventy two inbreds were used to capture a broad range of maturities. These inbreds were grouped into 6 maturity groups to simplify the dissection process (Table 2). Non-traited inbreds were chosen to avoid the complexity of conducting tassel dissections on regulated fields. This experiment reflects data collected at four different field locations: Williamsburg (IA), Waterman (IL), Farmer city (IL) and Constantine (MI). Four-row by twenty feet long plots were grown. Target final population was 38,000 plants per acre. Final stand counts were documented at V3 stage. The fifth and tenth leaves of three representative plants per plot were marked to keep track of V-stages; all leaves were counted including the coleoptiles. Three representative plants from each group were sampled at 60, 70, and 80% of average growth development units to flowering (defined as when approximately half of the tassels in that group were shedding pollen, represented as P50) and tassel dissections were performed as previously described.

TABLE 2

| | Maturity Group | | | | | |
|---|---|---|---|---|---|---|
| | Group 1 | Group 2 | Group 3 | Group 4 | Group 5 | Group 6 |
| Average GDU to P50% | 1200 | 1280 | 1330 | 1370 | 1420 | 1460 |
| First dissection | 720 | 768 | 798 | 822 | 852 | 876 |
| Second dissection | 840 | 896 | 931 | 959 | 994 | 1022 |
| Third dissection | 960 | 1024 | 1064 | 1096 | 1136 | 1168 |

Plants were chosen from the middle rows to avoid border plants. At the moment of the first sampling, plants at a consistent development stage were marked to be used for the second and third sampling. The dates of each dissection along with the V-stage at sampling times were documented. The tassel stage of development was identified following the Relative Development Scale as described above. Plots continued to be monitored through flowering and the date of P50 was registered. Vegetative stage varied across inbreds relative to tassel development stages. For example, V-stage at T5 (beginning of anther differentiation) ranged by more than 6.5 leaves across inbreds from 7 to 14 leaves. This was approximately 64% of the overall average of 10.3 leaves to reach that stage.

Example 7

Average GDU Relative to Tassel and Flower Development Stages

This example demonstrates that the average GDUs required to achieve a given tassel development stage or flower stage can vary significantly across genotypes and that GDU therefore is not a reliable predictor of tassel development. Data was taken from the field plots and inbred plants described above. Hourly temperatures from planting through flowering were monitored using Onset weather stations and data was used to calculate daily cumulative GDU following the traditional method (i.e., averaging daily maximum and minimum temperatures). Data from sampled dissections indicating tassel development stage were plotted against GDU requirements. Inbreds that differentiate a larger number of leaves are generally expected to have a larger GDU requirement in order to reach a specific tassel development stage. However, the variation observed in V-stages to T5 discussed above did not explain all the variation observed in GDU to T5. This could suggest that the phyllochron, defined as the time between the elongation of successive leaves, might vary between inbreds. The results of this study showed that GDU to achieve the T5 stage ranged by more than 400 heat or growing degree units across inbreds; about 40% of the overall average.

A strong correlation between the GDU requirements to P50 and to a given tassel development stage across inbred varieties was observed. Using data from the field plots and inbred plants, average GDU requirements to P50 were recorded across inbreds and compared at given tassel development stages. GDU requirements to P50 varied from 1283 to 1645 units, from the shortest to the longest maturity inbred; slightly over 360 GDU difference. These differences were found to correlate with differences in average GDU requirements to T5 stage within inbred lines (FIG. 5).

Example 8

Constructing a Relative Development Scale

This example demonstrates construction of a standardized scale for monitoring and/or predicting tassel development. This Relative Development Scale successfully standardized maize tassel development stages across inbreds.

Given the strong correlation between the GDU requirements to achieve P50 at a given Tassel development stage across inbred varieties as described above, the Relative Development Scale was developed. This was calculated by expressing tassel growth of each genotype relative to thermal time to Pollen Shed as follows:

Relative Development Scale=(GDU to $Tn$/GDU to $Px$)

Figure 7:
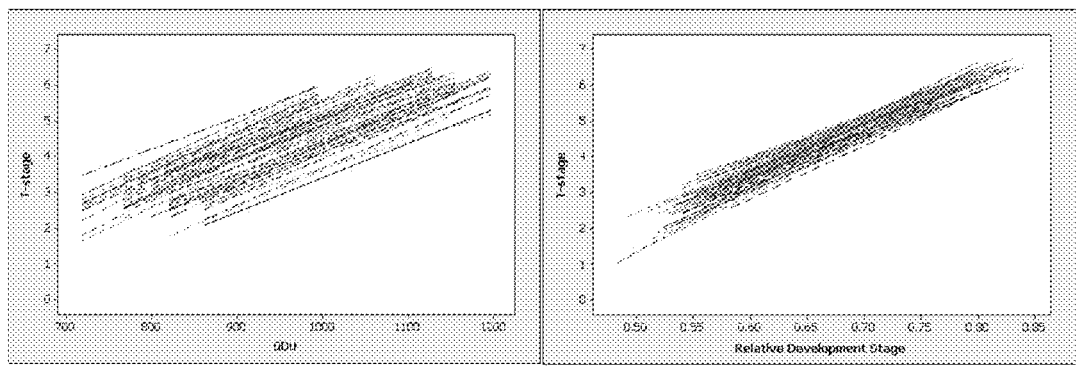
FIG. 7 illustrates T-stages as a function of GDU (A) and Relative Development Scale (B). Each regression line represents a different inbred.
Figure 8:
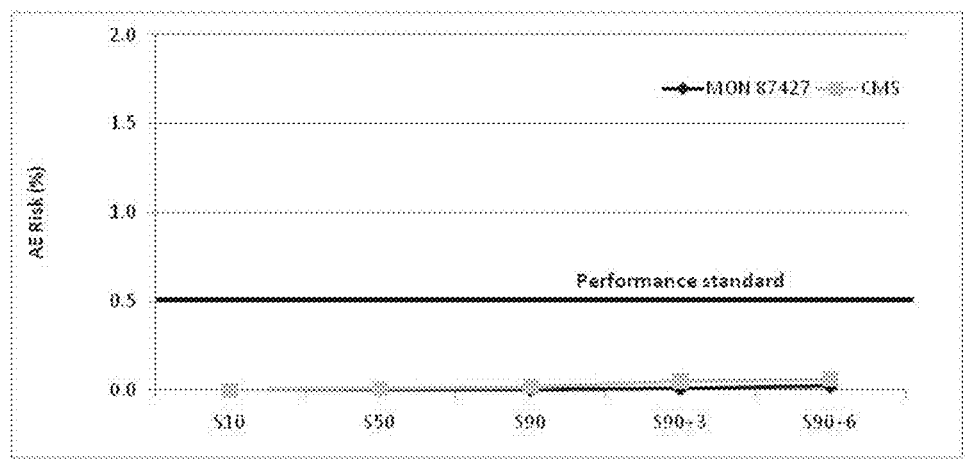
FIG. 8 illustrates the percentage of anther extrusion risk (y axis) measured at different silking stages (x axis) for MON 87427 and CMS blocks.
Figure 9:
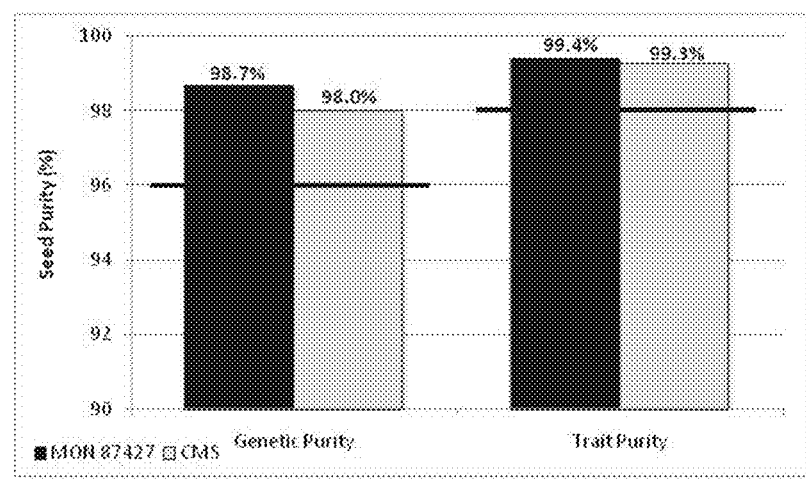
FIG. 9 illustrates the seed genetic purity and the seed trait purity of hybrid seed produced by MON 87427 with the Roundup® Hybridization System (RHS) and by the CMS system at the 95% significance level. The black line on the chart represents the desired quality standards for seed genetic purity and seed trait purity, respectively.

Data was used from the field plots and inbred plants described above. The GDU value at a given tassel development stage (GDU to Tn) was divided by the number of GDUs known to be required to achieve a particular stage of pollen shed (GDU to Px), which in this case was P50 for a certain genotype. This reconciled differences in tassel development stage across genotypes. For example, the GDU requirements to reach T5 were fairly consistent on the Relative Development Scale among all inbreds and only ranged from 69 to 75% of the GDU required to P50. Variation in regression lines of GDU requirements of various genotypes relative to Tassel development stage compared with the more consistent regression lines of those same genotypes using the standardized T-scale were used to assess standardization of the scale, regardless of maturity group (FIG. 7).

Example 9

Predicting Optimal Timing for Development Modulating Treatment

This example demonstrates use of the Relative Development Scale to determine the optimal timing for a chemical agent spraying regimen in order to achieve full maize tassel sterility. In this example the chemical agent was the glyphosate herbicide Roundup® used in combination with MON 87427 maize plants in the Roundup® Hybridization System (RHS). Optimal spraying time was correlated with actual tassel development stage and complete maize tassel sterility was achieved with only a single effective dose of Roundup®.

Thirty two inbred backgrounds comprising the MON 87427 event were selected for the study and grouped into two maturity groups. Inbreds were planted in twenty feet rows, with three feet alleys. Row spacing was 30 inches between plants. The rows were planted such that there were four rows of female "tester" plants followed by two rows of male pollinator plants. Transgenic events were selected for this study that had vegetative and female-tissue tolerance to glyphosate but not male-reproductive tissue tolerance (i.e., tissue-selective glyphosate tolerance). The male pollinators were also male tolerant to glyphosate, while the female recipient plants were male-sensitive when treated with glyphosate. Spraying treatments were blocked and sub-grouped in two based on the inbred maturity. Immediately before each spray, three representative plants from each plot were selected and dissected in the field. Tassel length, tassel development stage, date, and GDU at spray were recorded. Spray treatments (SS1) of Roundup PowerMAX™ with a water volume of 15 gallons/acre were applied once to each treatment's respective maturity group using a high clearance sprayer. Sterility Spray treatments were applied in a range from 50% through 80% of GDUs required to achieve P50 (averaged within inbred maturity group) as shown as shown in Table 3, where WC="Weed Control"; Trt 1 SS1=50% GDU to P50; Trt 2 SS1=57.5% GDU to P50; Trt 3 SS1=65% GDU to P50; Trt 4 SS1=72.5% GDU to P50; Trt 5 SS1=80% GDU to P50.

TABLE 3

| WC sprays = 22 oz/acre (0.75#ae/ac) | | | | | | |
|---|---|---|---|---|---|---|
| SS1 sprays = 33 oz/acre (1.25#ae/ac) | | | | | | |
| | Fahrenheit GDU (FGDU) | | | | | |
| | V3 | 650 | 750 | 850 | 950 | 1050 | 1150 |

| | | V3 | 650 | 750 | 850 | 950 | 1050 | 1150 |
|---|---|---|---|---|---|---|---|---|
| Trt 1 | Maturity 1 | WC | SS1 | | | | | |
| | Maturity 2 | WC | | SS1 | | | | |
| Trt 2 | Maturity 1 | WC | | SS1 | | | | |
| | Maturity 2 | WC | | | SS1 | | | |
| Trt 3 | Maturity 1 | WC | | | SS1 | | | |
| | Maturity 2 | WC | | | | SS1 | | |
| Trt 4 | Maturity 1 | WC | | | | SS1 | | |
| | Maturity 2 | WC | | | | | SS1 | |
| Trt 5 | Maturity 1 | WC | | | | | SS1 | |
| | Maturity 2 | WC | | | | | | SS1 |

Figure 6:
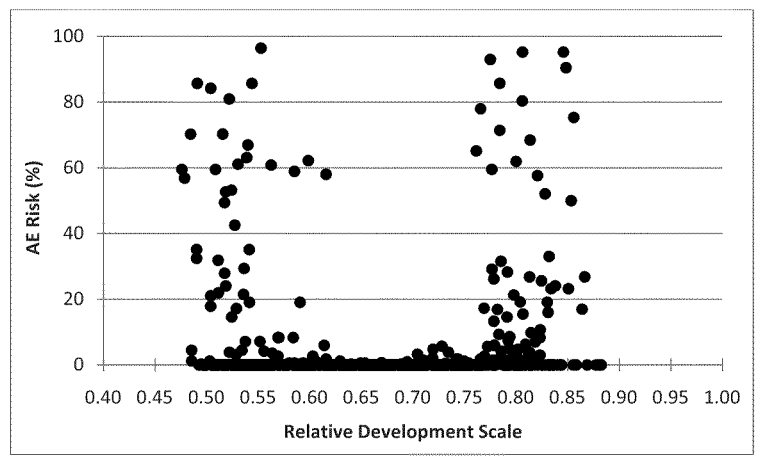
FIG. 6 illustrates an example of how the Relative Development Scale reveals an optimal window of chemical agent efficacy for producing maize tassel sterility as measured by anther extrusion risk (AE Risk (%)) which occurs at 0.62 and 0.75 on the Relative Development Scale, where 62%-75% of the total GDU requirement to reach P50 are reached and in which AE Risk is minimized across inbreds and maturity groups. Each data point represents averaged values for 1 plot, or two rows totally 32 plants. N=620

Following all spray treatments, tassel sterility/fertility assessments were conducted by evaluating anther extrusion and pollen shed relative to silk emergence. These evaluations were performed when each plot was at specific developmental stages: 10% of plants in entry with silk (S10); 50% of plants in entry with silk (S50); 90% of plants in entry with silk (S90); 3 days after S90 date (S90+3); and 6 days after S90 date (S90+6). Plants were observed for anther extrusion (AE)

and sterility was measured using an Anther Extrusion Risk index (AE Risk) which is a weighted average combining the percentage of plants in the plot showing anther extrusion with the intensity of the phenomena. For example, Light Partial (LP) is a tassel with 10 or fewer anthers extruding. Medium Partial (MP) is a tassel with >11 anthers up to 25% anthers extruding. Heavy Partial (HP) is a tassel which has >25% of anthers extruding. As shown in FIG. 6, the Relative Development Scale reveals an optimal window of chemical agent efficacy for producing maize tassel sterility between 0.62 and 0.75 in which AE Risk is minimized across inbreds and maturity groups. This study confirms the effectiveness of the Relative Development Scale as a tool to provide spraying recommendations for implementation of a Roundup® hybridization system across inbreds. This would be of particular use with MON 87427.

Example 10

Method of Hybrid Seed Production with Improved Seed Purity

Methods of hybrid seed production and the resulting seed purity were measured using twenty-four pilot production blocks at sites in Kearney, Nebr.; Williamsburg, Iowa; Waterman, Ill.; Farmer City, Ill.; and Constantine, Mich. Four MON 87427 blocks and two cytoplasmic tassel sterility (CMS) blocks were planted at each location. MON 87427 blocks consisted of 01DKD2MON87427-MON89034 female× 80IDM2MON88017 male, and CMS blocks consisted of 01DKD2NK603B-CMS female×80IDM2MON88017 male.

The planting pattern was a 4:1 female to male ratio on 30 inch rows. Each experimental block was ten by 100 to 150 feet long panels in size. Blocks were surrounded by 30 feet (12 rows) of male on the sides as well as on the front and back. Blocks were at least 200 feet away from other potential pollen sources and isolated from each other by 45 feet. The study was planted at a population of 40,000 and 38,000 for irrigated and non-irrigated land, respectively. Both the female and male rows were planted at the same time. The male rows were flamed at V3 growth stage to achieve stunting growth and delay pollen shed on the male plants by alternatively flaming 20 feet row length sections. Propane flamers were mounted behind a tractor and positioned over the male rows and alternated between flaming and non-flaming roughly every 20 feet. Insecticide was used at planting to minimize variability due to insect pressure. Male rows were destroyed following pollination. All blocks were sprayed with 0.75 lb a.e./acre of Roundup PowerMax™ around V3 for weed control purposes. In addition, the MON 87427 blocks were sprayed with two sprays at 0.75 lb a.e./acre of Roundup PowerMax™ applied at 825 and 975 growing degree units (GDU) from planting. The spray volume was held constant at 15 gallons per acre (GPA).

Tassel sterility was assessed by monitoring plants every other day from tassel emergence through 6 days after the end of silking (P90+6 days). If breakage (pollen shed) occurred, individual plants were further categorized as low pollen (LP; less than 10 anthers exposed), medium pollen (MP; 11 anthers up to 25% tassel surface area with anthers extruding), or high pollen (HP; more than 25% of tassel surface area with anthers extruding). An Anther Extrusion risk (AE Risk) was then calculated as:

$$\text{AE Risk }\%=([(LP\times0.25)+(MP\times0.5)+(HP\times1.0)]/\text{Stand count})\times100$$

After physiological maturity and around 30-35% kernels moisture content, a 100-ear composite sample per block was hand-harvested, following a pre-determined sampling scheme to represent all panels in the block. Samples were dried and weighted to adjust final yield. A first set of samples was hand treated and sent for quality analysis (cold germination and warm germination assessment using two 100-seed replications). A second set of samples was sent for genetic purity analysis (single nucleotide polymorphism (SNPs) analysis) and trait purity analysis (ELISA of male specific marker). A third set of samples was used to document seed size distribution. Pilot production blocks were combine-harvested and yield was adjusted to 15% moisture in the determination of bushel per acre.

Overall, both the CMS and MON 87427 blocks exceeded maize tassel sterility and seed purity standards. Anther extrusion risk was well below the desired performance standard of 0.5% even 6 days after 90% of the female population had exerted silks (FIG. 8). Hardly any breakage was documented on MON 87427 blocks, but a slightly higher breakage rate at late silking stages was observed on CMS blocks. Both the female and male maize parent plants for CMS and MON 87427 were tested for genetic purity and results showed 100% purity. The high levels of maize tassel sterility of both the MON 87427 and the CMS parent plants produced high levels of genetic purity and trait purity in the hybrid seed produced from these trials (FIG. 9). There was no statistically significant difference for trait purity between MON 87427 and CMS, but a statistically significant difference (at $p<0.05$) was measured for genetic purity between MON 87427 and CMS. The genetic purity level of hybrid seed produced using MON 87427 and the Roundup® Hybridization System (RHS) was 98.7%, which was significantly higher than the genetic purity level of hybrid seed produced using CMS (98.0%). This resulted in the female MON 87427 parent plants producing about 0.2% less 'selfs' and 0.5% less 'others' than the CMS system parent plants, demonstrating that that use of MON 87427 with the Roundup® Hybridization System (RHS) may be used to improve maize seed purity in maize hybrid seed production.

A deposit of a representative sample of MON 87427 seed disclosed above and recited in the claims has been made under the Budapest Treaty with the American Type Culture Collection (ATCC), 10801 University Boulevard, Manassas, Va. 20110. The ATCC accession number for this deposit is PTA-7899. The deposit will be maintained in the depository for a period of 30 years, or 5 years after the last request, or for the effective life of the patent, whichever is longer, and will be replaced as necessary during that period.

Having illustrated and described the principles of the invention, it should be apparent to persons skilled in the art that the invention can be modified in arrangement and detail without departing from such principles. We claim all modifications that are within the spirit and scope of the appended claims.

We claim:

1. A recombinant DNA molecule comprising a nucleotide sequence selected from the group consisting of SEQ ID NO: 1-8, SEQ ID NO: 10 and full complements thereof.

2. The recombinant DNA molecule of claim 1, wherein said recombinant DNA molecule is formed by the junction of an inserted heterologous nucleic acid molecule and genomic DNA of a maize plant, plant cell, or seed.

3. The recombinant DNA molecule of claim 1, wherein said DNA molecule is from a transgenic maize plant comprising event MON 87427, a representative sample of seed comprising said event having been deposited as ATCC PTA-7899.

4. The recombinant DNA molecule of claim 1, wherein said DNA molecule is an amplicon diagnostic for the presence of DNA from transgenic maize event MON 87427.

5. The recombinant DNA molecule of claim 1, wherein said recombinant DNA molecule is in a maize plant, plant cell, seed, progeny plant, plant part, or commodity product.

6. A DNA probe comprising a nucleotide sequence of sufficient length of contiguous nucleotides of SEQ ID NO: 10, or a full complement thereof, to function as a DNA probe that hybridizes under stringent hybridization conditions with a DNA molecule comprising a nucleotide sequence selected from the group consisting of SEQ ID NO: 1-8 and SEQ ID NO: 10 and does not hybridize under the stringent hybridization conditions with a DNA molecule not comprising a nucleotide sequence selected from the group consisting of SEQ ID NO: 1-8 and SEQ ID NO: 10, and wherein said DNA probe comprises the nucleotide sequence of SEQ ID NO: 1 or SEQ ID NO: 2.

7. A pair of DNA molecules comprising a first DNA molecule and a second DNA molecule different from the first DNA molecule, wherein said first and second DNA molecules each comprise a nucleotide sequence of sufficient length of contiguous nucleotides of SEQ ID NO: 10, or a full complement thereof, and wherein said first DNA molecule resides in a transgene insert DNA sequence of SEQ ID NO: 10, and said second DNA molecule resides in the maize genomic DNA sequence of SEQ ID NO: 10, to function as DNA primers when used together in an amplification reaction with DNA from event MON 87427 to produce an amplicon diagnostic for transgenic maize event MON 87427 DNA in a sample, and wherein said amplicon comprises the nucleotide sequences of SEQ ID NO: 1 or SEQ ID NO: 2.

8. A method of detecting the presence of a DNA molecule from a transgenic maize plant comprising event MON 87427 in a sample, said method comprising:
   a) contacting said sample with the DNA probe of claim 6;
   b) subjecting said sample and said DNA probe to stringent hybridization conditions; and
   c) detecting hybridization of said DNA probe to a DNA molecule in said sample, wherein the hybridization of said DNA probe to said DNA molecule indicates the presence of a DNA molecule from a transgenic maize plant comprising event MON 87427 in said sample.

9. A method of detecting the presence of a DNA molecule from a transgenic maize plant comprising event MON 87427 in a sample, said method comprising:
   a) contacting said sample with the pair of DNA molecules of claim 7;
   b) performing an amplification reaction sufficient to produce a DNA amplicon comprising a sequence selected from the group consisting of SEQ ID NO: 1-8 and SEQ ID NO: 10; and
   c) detecting the presence of said DNA amplicon in said reaction, wherein the presence of said DNA amplicon in said reaction indicates the presence of a DNA molecule from a transgenic maize plant comprising event MON 87427 in said sample.

10. A DNA kit comprising:
   a) a pair of DNA molecules comprising a first DNA molecule and a second DNA molecule different from the first DNA molecule, wherein said first and second DNA molecules each comprise a nucleotide sequence of sufficient length of contiguous nucleotides of SEQ ID NO: 10, or a full complement thereof, and wherein said first DNA molecule resides in a transgene insert DNA sequence of SEQ ID NO: 10, and said second DNA molecule resides in the maize genomic DNA sequence of SEQ ID NO: 10, to function as DNA primers when used together in an amplification reaction with DNA from event MON 87427 to produce an amplicon diagnostic for transgenic maize event MON 87427 DNA in a sample, and wherein said amplicon comprises the nucleotide sequences of SEQ ID NO: 1 or SEQ ID NO: 2; or
   b) at least one DNA probe diagnostic for event MON 87427, wherein the DNA probe comprises the nucleotide sequence of SEQ ID NO: 1 or SEQ ID NO: 2.

11. A recombinant maize plant, seed, cell, or plant part thereof comprising the nucleotide sequence of SEQ ID NO: 1 and SEQ ID NO: 2 and a nucleic acid molecule encoding a CP4-EPSPS.

12. The recombinant maize plant, seed, cell, or plant part thereof of claim 11, wherein said plant, seed, cell, or plant part thereof has tissue-selective tolerance to glyphosate herbicide treatment.

13. The recombinant maize plant, seed, cell, or plant part thereof of claim 11, the genome of which produces an amplicon comprising a DNA molecule selected from the group consisting of SEQ ID NO: 1-8 and SEQ ID NO: 10 when tested in a DNA amplification method.

14. A maize plant or seed, comprising event MON 87427, a representative sample of seed comprising said event having been deposited under ATCC accession No. PTA-7899.

15. The maize plant or seed of claim 14, wherein said maize plant or seed is a hybrid having at least one parent comprising event MON 87427.

16. A nonliving plant material comprising the nucleotide sequence of SEQ ID NO: 1 and SEQ ID NO: 2 and a nucleic acid molecule encoding a CP4-EPSPS.

17. A microorganism comprising the nucleotide sequence of SEQ ID NO: 1 and SEQ ID NO: 2 and a nucleic acid molecule encoding a CP4-EPSPS.

18. The microorganism of claim 17, wherein said microorganism is a plant cell.

19. A commodity product produced from a transgenic maize plant comprising event MON 87427 and comprising the recombinant DNA molecule of claim 1, wherein detection of said nucleotide sequence in a sample derived from said commodity product is determinative that said commodity product was produced from said transgenic maize plant comprising event MON 87427.

20. The commodity product of claim 19, wherein said commodity product is selected from the group consisting of whole or processed seeds, animal feed, oil, meal, flour, flakes, bran, biomass, and fuel products.

21. A method of producing the commodity product of claim 19, said method comprising:
   a) obtaining a maize plant or part thereof comprising transgenic maize event MON 87427; and
   b) producing a maize commodity product from the maize plant or part thereof.

22. A method for controlling weeds in a field comprising planting transgenic maize plants comprising event MON 87427 in a field and applying an effective dose of glyphosate herbicide to control weeds in said field without injuring said transgenic maize plants comprising event MON 87427.

23. The method of claim 22, wherein said effective dose of glyphosate herbicide is from about 0.1 pound to about 4 pounds per acre.

24. A method of producing a maize plant that tolerates application of glyphosate herbicide comprising:
   a) sexually crossing a transgenic maize plant comprising event MON 87427 comprising a nucleic acid molecule comprising a nucleotide sequence selected from the group consisting of SEQ ID NO: 10 with a second maize plant, thereby producing seed;
   b) collecting said seed produced from said cross;

c) growing said seed to produce a plurality of progeny plants;
d) treating said progeny plants with glyphosate; and
e) selecting a progeny plant that is tolerant to glyphosate.

25. A method of producing a maize plant that tolerates application of glyphosate herbicide comprising:
  a) selfing a transgenic maize plant comprising event MON 87427 comprising a nucleic acid molecule comprising a nucleotide sequence selected from the group consisting of SEQ ID NO: 1-8 and SEQ ID NO: 10, thereby producing seed;
  b) collecting said seed produced from said selfing;
  c) growing said seed to produce a plurality of progeny plants;
  d) treating said progeny plants with glyphosate; and
  e) selecting a progeny plant that is tolerant to glyphosate.

26. A method of producing hybrid maize seed comprising:
  a) planting transgenic maize seed comprising event MON 87427 in an area;
  b) growing a maize plant from said seed;
  c) treating said plant with an effective dose of glyphosate herbicide prior to pollen formation to make said plant male sterile without injuring said plant;
  d) fertilizing said plant with pollen from a second parent plant; and
  e) harvesting seed from said plant, wherein said seed is hybrid maize seed produced by the cross of a transgenic maize plant comprising event MON 87427 with a second parent plant.

27. The method of claim 26, wherein said effective dose of glyphosate herbicide is from about 0.1 pound to about 4 pounds per acre.

28. The method of claim 26, further comprising planting a second parent plant seed in said area and growing a maize plant from said second parent plant.

29. The method of claim 28, wherein said second parent plant is glyphosate tolerant.

* * * * *